(12) United States Patent
Beatty et al.

(10) Patent No.: US 11,360,100 B2
(45) Date of Patent: Jun. 14, 2022

(54) METHODS AND COMPOSITIONS USEFUL IN DETECTING PROTEINS

(71) Applicant: OREGON HEALTH & SCIENCE UNIVERSITY, Portland, OR (US)

(72) Inventors: Kimberly Beatty, Portland, OR (US); Hannah Zane, Portland, OR (US); Julia Doh, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 294 days.

(21) Appl. No.: 16/347,768

(22) PCT Filed: Nov. 8, 2017

(86) PCT No.: PCT/US2017/060609
§ 371 (c)(1),
(2) Date: May 6, 2019

(87) PCT Pub. No.: WO2018/089472
PCT Pub. Date: May 17, 2018

(65) Prior Publication Data
US 2019/0383824 A1     Dec. 19, 2019

Related U.S. Application Data

(60) Provisional application No. 62/419,285, filed on Nov. 8, 2016.

(51) Int. Cl.
*G01N 33/68*     (2006.01)
*C07K 14/74*     (2006.01)
*C07K 14/705*     (2006.01)
*G01N 33/566*     (2006.01)

(52) U.S. Cl.
CPC ... *G01N 33/6872* (2013.01); *C07K 14/70539* (2013.01); *C07K 14/70582* (2013.01); *G01N 33/566* (2013.01); *G01N 33/68* (2013.01); *C07K 2319/035* (2013.01); *C07K 2319/10* (2013.01); *C07K 2319/21* (2013.01); *C07K 2319/60* (2013.01)

(58) Field of Classification Search
None
See application file for complete search history.

(56) References Cited

FOREIGN PATENT DOCUMENTS

| WO | 2007062466 | 6/2007 |
| WO | 2018089472 | 5/2018 |

OTHER PUBLICATIONS

Lotze et al., "Peptide-Tags for Site-Specific Protein Labelling in Vitro and in Vivo", Molecular BioSystem, vol. 12, No. 6, Jun. 2016, pp. 1731-2012.
PCT/US2017/060609, "International Search Report and Written Opinion", dated Mar. 13, 2018, 14 pages.
PCT/US2017/060609, "Invitation to Pay Add'l Fees and Partial Search Rpt", dated Jan. 22, 2018, 2 pages.
Tsutsumi et al., "Fluorogenically Active Leucine Zipper Peptides as Tag-Probe Pairs for Protein Imaging in Living Cells", Angewandte Chemie, vol. 48, No. 48, Oct. 28, 2009, pp. 9164-9166.
PCT/US2017/060609, "International Preliminary Report on Patentability", dated May 23, 2019, 10 pages.

*Primary Examiner* — Kagnew H Gebreyesus
(74) *Attorney, Agent, or Firm* — Kilpatrick Townsend & Stockton LLP

(57) ABSTRACT

Disclosed herein are compositions, reagents, and methods that can be used to observe multiple targets. The targets can be observed using a variety of methods, for example, by fluorescence, EM, and CLEM. The systems and methods involve the use of self-sorting coiled-coil heterodimers that label multiple proteins in a sample. These compositions, interchangeably termed "VIP tags" herein can be used to efficiently label cellular proteins with high specificity.

10 Claims, 18 Drawing Sheets
Specification includes a Sequence Listing.

Figure 16
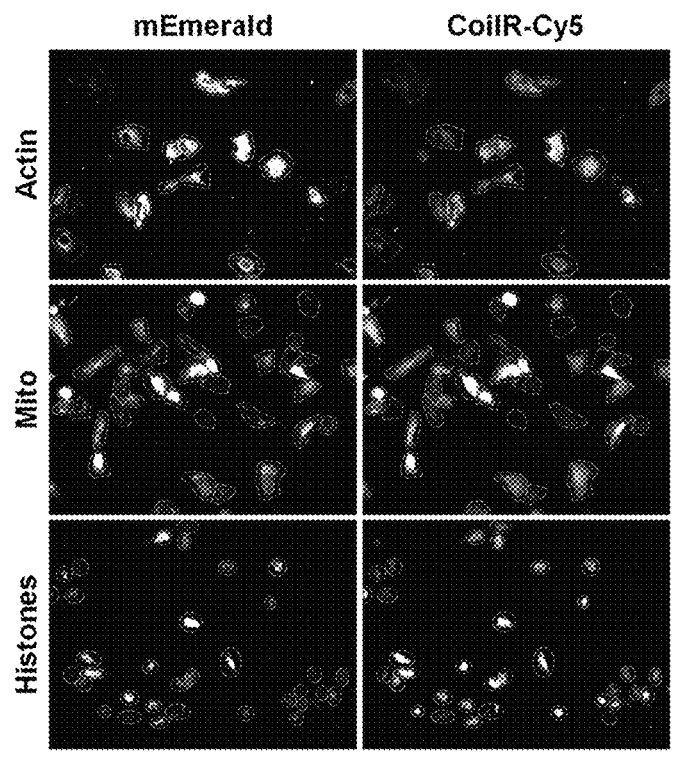
| | Pearson's corr. | Std. dev. | Cells analyzed |
|---|---|---|---|
| Actin-CoilE | 0.97 | 0.02 | 15 |
| Mitochondria-CoilE | 0.89 | 0.08 | 39 |
| Histones-CoilE | 0.90 | 0.10 | 34 |
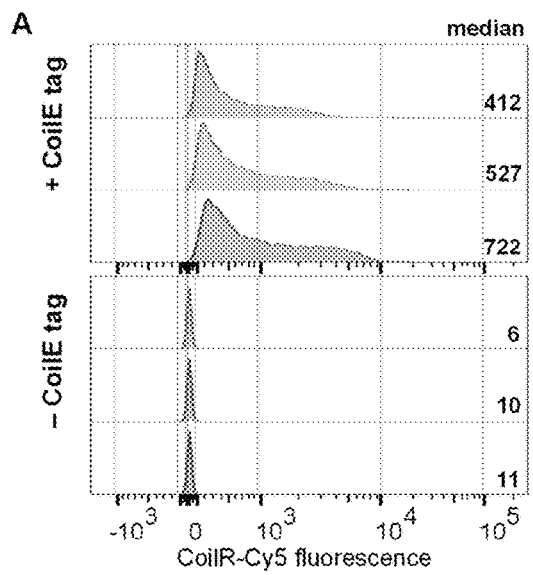
Figure 17A
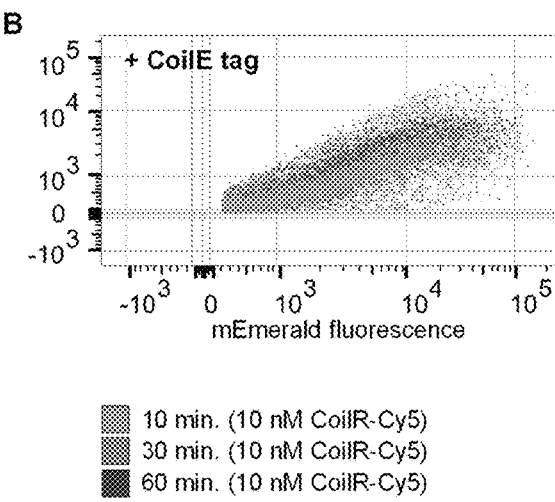
Figure 17B

SEQUENCE LISTING

```
<160> NUMBER OF SEQ ID NOS: 14

<210> SEQ ID NO 1
<211> LENGTH: 43
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 1

Leu Glu Ile Arg Ala Ala Phe Leu Arg Gln Arg Asn Thr Ala Leu Arg
1               5                   10                  15

Thr Glu Val Ala Glu Leu Glu Gln Glu Val Gln Arg Leu Glu Asn Glu
            20                  25                  30

Val Ser Gln Tyr Glu Thr Arg Tyr Gly Pro Leu
        35                  40

<210> SEQ ID NO 2
<211> LENGTH: 43
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 2

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Arg
            20                  25                  30

Val Ser Gln Tyr Arg Thr Arg Tyr Gly Pro Leu
        35                  40

<210> SEQ ID NO 3
<211> LENGTH: 47
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 3

Asn Leu Val Ala Gln Leu Glu Asn Glu Val Ala Ser Leu Glu Asn Glu
1               5                   10                  15

Asn Glu Thr Leu Lys Lys Lys Asn Leu His Lys Lys Asp Leu Ile Ala
            20                  25                  30

Tyr Leu Glu Lys Glu Ile Ala Asn Leu Arg Lys Lys Ile Glu Glu
        35                  40                  45

<210> SEQ ID NO 4
```

```
<211> LENGTH: 50
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 4

Ala Arg Asn Ala Tyr Leu Arg Lys Lys Ile Ala Arg Leu Lys Lys Asp
1               5                   10                  15

Asn Leu Gln Leu Glu Arg Asp Glu Gln Asn Leu Glu Lys Ile Ile Ala
            20                  25                  30

Asn Leu Arg Asp Glu Ile Ala Arg Leu Glu Asn Glu Val Ala Ser His
        35                  40                  45

Glu Gln
    50

<210> SEQ ID NO 5
<211> LENGTH: 42
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 5

Asn Glu Val Thr Thr Leu Glu Asn Asp Ala Ala Phe Ile Glu Asn Glu
1               5                   10                  15

Asn Ala Tyr Leu Glu Lys Glu Ile Ala Arg Leu Arg Lys Glu Lys Ala
            20                  25                  30

Ala Leu Arg Asn Arg Leu Ala His Lys Lys
        35                  40

<210> SEQ ID NO 6
<211> LENGTH: 54
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 6

Gln Lys Val Ala Glu Leu Lys Asn Arg Val Ala Val Lys Leu Asn Arg
1               5                   10                  15

Asn Glu Gln Leu Lys Asn Lys Val Glu Glu Leu Lys Asn Arg Asn Ala
            20                  25                  30

Tyr Leu Lys Asn Glu Leu Ala Thr Leu Glu Asn Glu Val Ala Arg Leu
        35                  40                  45

Glu Asn Asp Val Ala Glu
    50

<210> SEQ ID NO 7
<211> LENGTH: 44
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

Asn Thr Val Lys Glu Leu Lys Asn Tyr Ile Gln Glu Leu Glu Glu Arg
1               5                   10                  15

Asn Ala Glu Leu Lys Asn Leu Lys Glu His Leu Lys Phe Ala Lys Ala
            20                  25                  30

Glu Leu Glu Phe Glu Leu Ala Ala His Lys Phe Glu
        35                  40
```

```
<210> SEQ ID NO 8
<211> LENGTH: 54
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 8

Gln Lys Val Ala Gln Leu Lys Asn Arg Val Ala Tyr Lys Leu Lys Glu
1               5                   10                  15

Asn Ala Lys Leu Glu Asn Ile Val Ala Arg Leu Glu Asn Asp Asn Ala
                20                  25                  30

Asn Leu Glu Lys Asp Ile Ala Asn Leu Glu Lys Asp Ile Ala Asn Leu
            35                  40                  45

Glu Arg Asp Val Ala Arg
        50

<210> SEQ ID NO 9
<211> LENGTH: 36
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 9

Leu Glu Ile Arg Val Ala Phe Leu Arg Gln Arg Asn Thr Ala Leu Arg
1               5                   10                  15

Thr Glu Val Ala Glu Leu Glu Gln Glu Val Gln Arg Leu Glu Asn Arg
                20                  25                  30

Tyr Gly Pro Leu
        35

<210> SEQ ID NO 10
<211> LENGTH: 36
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 10

Leu Glu Ile Glu Ala Ala Phe Leu Glu Arg Glu Asn Thr Ala Leu Glu
1               5                   10                  15

Thr Arg Val Ala Glu Leu Arg Gln Arg Val Gln Arg Leu Arg Asn Glu
                20                  25                  30

Tyr Gly Pro Leu
        35

<210> SEQ ID NO 11
<211> LENGTH: 68
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 11

Met Gly Gly Ser Leu Glu Ile Arg Ala Ala Phe Leu Arg Gln Arg Asn
1               5                   10                  15

Thr Ala Leu Arg Thr Glu Val Ala Glu Leu Glu Gln Glu Val Gln Arg
                20                  25                  30

Leu Glu Asn Glu Val Ser Gln Tyr Glu Thr Arg Tyr Gly Pro Leu Gly
            35                  40                  45
```

```
Gly Gly Ala Ala Ala Leu Gly Cys Leu Ala Ala Leu Glu His His
    50                  55                  60
His His His His
 65

<210> SEQ ID NO 12
<211> LENGTH: 68
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 12

Met Gly Gly Ser Leu Glu Ile Arg Ala Ala Phe Leu Arg Gln Arg Asn
  1               5                  10                  15

Thr Ala Leu Arg Thr Glu Val Ala Glu Leu Gln Glu Val Gln Arg
                20                  25                  30

Leu Glu Asn Glu Val Ser Gln Tyr Glu Thr Arg Tyr Gly Pro Leu Gly
                35                  40                  45

Gly Gly Ala Ala Ala Leu Gly Lys Leu Ala Ala Leu Glu His His
    50                  55                  60
His His His His
 65

<210> SEQ ID NO 13
<211> LENGTH: 70
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 13

Met Gly Ser Ser Asn Thr Val Lys Glu Leu Lys Asn Tyr Ile Gln Glu
  1               5                  10                  15

Leu Glu Glu Arg Asn Ala Glu Leu Lys Asn Leu Lys Glu His Leu Lys
                20                  25                  30

Phe Ala Lys Ala Glu Leu Glu Phe Glu Leu Ala Ala His Lys Phe Glu
                35                  40                  45

Gly Gly Gly Ala Ala Ala Cys Leu Gly Lys Leu Ala Ala Leu Glu
    50                  55                  60
His His His His His His
 65                  70

<210> SEQ ID NO 14
<211> LENGTH: 80
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 14

Met Gly Ser Ser Gln Lys Val Ala Gln Leu Lys Asn Arg Val Ala Tyr
  1               5                  10                  15

Lys Leu Lys Glu Asn Ala Lys Leu Glu Asn Ile Val Ala Arg Leu Glu
                20                  25                  30

Asn Asp Asn Ala Asn Leu Glu Lys Asp Ile Ala Asn Leu Glu Lys Asp
                35                  40                  45
```

```
Ile Ala Asn Leu Glu Arg Asp Val Ala Arg Gly Gly Gly Ala Ala Ala
        50                  55                  60

Cys Leu Gly Lys Leu Ala Ala Ala Leu Glu His His His His His His
65                  70                  75                  80
```

METHODS AND COMPOSITIONS USEFUL IN DETECTING PROTEINS

CROSS REFERENCE TO RELATED APPLICATION

This application claims priority to U.S. Provisional Application No. 62/419,285, filed Nov. 8, 2016, which is incorporated by reference herein in its entirety.

BACKGROUND

Fluorescent tagging of proteins enables studies on protein function, interactions, dynamics and sub-cellular localization. The many genetically encoded fluorescent proteins (e.g., GFP or mCherry) are widely used tools for cellular imaging. However, the large size of these tags (~28 kDa) can influence protein function and localization and their photophysical properties are generally inferior to organic fluorophores. There are protein fusion tags for attaching an organic fluorophore to a protein of interest such as SNAP, TMP, Halo, and FAPs. Yet all of these tags are large (18-33 kDa), thus offering only modest improvement over fluorescent protein fusions.

Peptide tags enable fluorophore labeling without substantial weight. The tetracysteine biarsenical tag, which is comprised of just six amino acids, is representative of this class. Unfortunately, this tag can induce toxicity and non-specific labeling is often significant. Another approach exploits enzymatic catalysis to append biotin, coumarin, or resorufin to a short (<2 kDa) recognition sequence. Yet, development of each of these peptide tags involved masterful protein engineering and lacks the accessibility of fluorescent proteins. In over 15 years of community development, there are few versatile peptide tags and little spectral diversity compared to the array of fluorescent proteins.

Advances in electron microscopy (EM) and correlative light and EM (CLEM) present a new opportunity for directly probing the sub-cellular organization of macromolecular complexes. EM enables nanoscale biology ("nanobiology") to be investigated against a detailed backdrop of sub-cellular architectures. Many fields will be impacted by improved EM investigations of protein assemblies, including systems biology, neuroscience, infectious disease, and others. However, progress in EM imaging has been limited by the lack of good reporter tags. Without genetically-encoded EM tags, it remains challenging to image specific proteins and targets using EM.

A few genetically-encoded protein tags have been developed for EM. These include APEX; a tetracysteine tag, miniSOG; and FLIPPER. These tags all use diaminobenzidine (DAB) oxidation to form an insoluble polymer, which is subsequently stained to generate contrast. DAB precipitation is technically difficult to control and resolution is variable. On top of that, all of these tags use the same contrast chemistry. Therefore, they are monochromatic and can be used to label only one target at a time.

The majority of EM studies are reliant on immunolabeling with Qdot- or gold-conjugated antibodies. Immunolabeling has many drawbacks. First, the large size of antibodies reduces localization precision by more than 20 nm. In addition, low abundance proteins and rare interactions are difficult to see because the immunolabeling can be inefficient. As a result, antibodies have been implicated in the "reproducibility crisis" due to a combination of poor target specificity and a failure of researchers to validate their antibodies. Finally, immunolabeling protocols can alter or destroy fine structures within a cell that can be visualized with electron microscopy (a.k.a. ultrastructure). As a result, there have been relatively few high-resolution studies assessing more than one or two protein targets using EM or CLEM. One such study described the use of Qdot-conjugated antibodies for three-color CLEM, but this was a rare example of multi-color EM.

SUMMARY

Disclosed herein are compositions, reagents, and methods that can be used to observe multiple targets. The targets can be observed using a variety of methods, for example, by fluorescence, EM, and CLEM. The systems and methods involve the use of self-sorting coiled-coil heterodimers that label multiple proteins in a sample. These compositions, interchangeably termed "VIP tags" herein can be used to efficiently label cellular proteins with high specificity but are sufficiently small in size to maintain protein folding, function, and localization.

Disclosed are methods of visualizing one or more proteins of interest using VIP tags. These methods involve expressing a tagged protein of interest. The tagged protein of interest comprises the protein of interest and a polypeptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9 and SEQ ID NO:10. The method further involves contacting the tagged protein of interest with a peptide probe. The peptide probe comprises a label and forms a heterodimer with the polypeptide on the tagged protein. For example, the peptide probe would be a polypeptide comprising SEQ ID NO: 1 if the first tagged protein of interest comprises SEQ ID NO: 2; SEQ ID NO: 2 if the first tagged protein of interest comprises SEQ ID NO: 1; SEQ ID NO: 3 if the first tagged protein of interest comprises SEQ ID NO: 4; SEQ ID NO: 4 if the first tagged protein of interest comprises SEQ ID NO: 3; SEQ ID NO: 5 if the first tagged protein of interest comprises SEQ ID NO: 6; SEQ ID NO: 6 if the first tagged protein of interest comprises SEQ ID NO: 5; SEQ ID NO: 7 if the first tagged protein of interest comprises SEQ ID NO: 8; SEQ ID NO: 8 if the first tagged protein of interest comprises SEQ ID NO: 7; SEQ ID NO: 9 if the first tagged protein of interest comprises SEQ ID NO:10; and SEQ ID NO:10 if the first tagged protein of interest comprises SEQ ID NO:9. The method further involves visualizing a first label and in so doing, visualizing the protein of interest.

Optionally, the tagged protein of interest and/or the peptide probe may further comprise one or more modifications such as a cellular localization peptide, a cell penetrating peptide, a purification tag, a modification that facilitates covalent attachment of a label, or any other modification.

The peptide probes can include one or more labels. The label can be any label including, but not limited to, a fluorescent small molecule, a fluorescent protein, a quantum dot, a gold nanoparticle, a sensor (e.g., pH, metal, or redox sensor), a photoxidizer (e.g., eosin for DAB-dependent labeling), biotin, streptavidin, radionuclide, spin label, lanthanide chelator (e.g., gadolinium for MRI), or any other appropriate label for visualization.

The peptide probe can include more than one label. For example, the peptide probe can include two fluorescent molecules, a nanoparticle and a fluorophore, a fluorophore and a drug, or biotin and a pH sensor.

Expression of the first tagged protein of interest can occur in vitro or in a cell such as a mammalian cell. Expression of the first tagged protein of interest in a mammalian cell can occur in the context of a transfected cell line, a genetically-modified cell line, or a transgenic mouse.

Optionally, the methods described allow for visualizing more than one protein of interest. Visualizing a subsequent protein of interest can occur by any methodology including immunolabeling, expression of the second protein of interest in conjunction with a protein tag, or by expressing a second VIP-tagged protein of interest and tagging it with its cognate second peptide probe as described herein.

Disclosed herein are peptide probes comprising a polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10 and a label. The label can be any appropriate label including but not limited to a fluorescent small molecule, a fluorescent protein, a quantum dot, a gold nanoparticle, streptavidin, or biotin. The peptide probe can further include one or more modifications such as a cellular localization peptide, a purification tag, a chemical handle that facilitates covalent attachment of a label, or any other modification. The label can be added post-translationally.

Disclosed herein are expression vectors comprising a polynucleotide that encodes a polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9, or SEQ ID NO:10, a promoter operably linked to the first polynucleotide. Optionally, the expression vector includes a polynucleotide that encodes a polypeptide that aids in the selection of a cell that is positive for the expression vector, e.g., a selection marker. The expression vector can further include a polynucleotide that encodes a purification tag such as a His-tag. The expression vector can further include a protein label such as a fluorescent protein or streptavidin. The expression vector can further include a multiple cloning site to facilitate cloning of the protein of interest as a fusion with the polynucleotide of SEQ ID NOs: 1, 2, 3, 4, 5, 6, 7, 8, 9 or 10. The expression vector can also include a polynucleotide that encodes a protein of interest. The promoter can be any promoter including an exogenous promoter, a tissue specific promoter, or constitutively active promoter. The expression vector can further comprise one or more regulators of expression that limit expression to one or more particular tissues such as a transcriptional enhancer, transcriptional suppressor, or microRNA recognition element.

Disclosed herein are kits that include (i) an expression vector comprising a first polynucleotide that encodes a first polypeptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9 or SEQ ID NO:10; a promoter operably linked to the first polynucleotide; and (ii) a peptide probe that comprises a first polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9 or SEQ ID NO:10 and a label; provided that if the first expression vector comprises a polynucleotide encoding SEQ ID NO: 1, the first peptide probe comprises a polypeptide of SEQ ID NO: 2; if the first expression vector comprises a polynucleotide encoding SEQ ID NO: 2, the first peptide probe comprises a polypeptide of SEQ ID NO: 1; if the first expression vector comprises a polynucleotide encoding SEQ ID NO: 3, the first peptide probe comprises a polypeptide of SEQ ID NO: 4; if the first expression vector comprises a polynucleotide encoding SEQ ID NO: 4, the first peptide probe comprises a polypeptide of SEQ ID NO: 3; if the first expression vector comprises a polynucleotide encoding SEQ ID NO: 5, the first peptide probe comprises a polypeptide of SEQ ID NO: 6; if the first expression vector comprises a polynucleotide encoding SEQ ID NO: 6, the first peptide probe comprises a polypeptide of SEQ ID NO: 5; if the first expression vector comprises a polynucleotide encoding SEQ ID NO: 7, the first peptide probe comprises a polypeptide of SEQ ID NO: 8; if the first expression vector comprises a polynucleotide encoding SEQ ID NO: 8, the first peptide probe comprises a polypeptide of SEQ ID NO: 7; if the first expression vector comprises a polynucleotide encoding SEQ ID NO:9, the first peptide probe comprises SEQ ID NO:10; and if the first expression vector comprises a polynucleotide encoding SEQ ID NO:10, the first peptide probe comprises SEQ ID NO:9. Optionally, the first expression vector further comprises a third polynucleotide encoding a protein of interest linked to the first polynucleotide.

The kits can further comprise a label and posttranslational labeling reagent that conjugates the label to the peptide probe. The label can be any label, including a fluorescent small molecule, a fluorescent protein, a quantum dot, a gold nanoparticle, a sensor (e.g., pH, metal, or redox sensor), a photoxidizer (e.g., eosin for DAB-dependent labeling), biotin, streptavidin, radionuclide, spin label, lanthanide chelator (e.g., gadolinium for MRI), or any other appropriate label for visualization.

The kits can further comprise a second expression vector and a second peptide probe in combinations as described herein.

BRIEF DESCRIPTION OF THE SEVERAL VIEWS OF THE DRAWINGS

(FIG. 8B). Arrow heads indicate gold particles, PM=plasma membrane, M=mitochondria; ser/rer=smooth or rough endoplasmic reticulum; L=lysozyme. Scale bars indicate 100 nm.

FIG. 16 are images showing VIP E/R-tagged proteins show good correlation between fluorescence signal from mEmerald and the fluorescent signal from CoilR-Cy5. U-2 OS cells were transfected with vectors encoding mEmerald-CoilE-Actin-C18 (top), mEmerald-CoilE-mito (middle), or mEmerald-CoilE-H2B (bottom). Post-fixation, targets were detected by treatment with CoilR-Cy5. (Left) Pearson's correlation values (p) are given as averages of individual cells (single slices taken at 20×, min. n=15, see description). Regions of interest used to calculate values are shown as dashed lines in the micrographs.

FIGS. 17A and 17B are data from flow cytometry analysis of cells expressing CoilE-tagged actin compared to untagged actin. U-2 OS cells were transfected with vectors encoding mEmerald-CoilE-Actin-C18. Post-fixation and permeabilization, targets were detected by treatment with CoilR-Cy5 probe-peptide at 10 nM for 10, 30, or 60 minutes at room temperature. Cells were gated using scatter and only green-fluorescent (transfected) cells were analyzed. Median fluorescence values (Cy5) are provided in 17A. These graphs show VIP E/R-tagged (Actin) proteins are selectively labeled after only 10 min with 10 nM CoilR-Cy5, analyzed by flow cytometry. Longer labeling times did not significantly improve labeling, suggesting labeling times greater than ca. 10 minutes are not necessary.

In FIG. 20A, CHOTRVb cells were transfected with tagged receptor (TfR1-CoilE) or untagged receptor (TfR1). Transfected cells were labeled with CoilR-Cy5 (100 nM) for 30 min. at 4° C. Cells were returned to 37° C. for 0 or 30 minutes and then were fixed and permeabilized. Fixed cells were immunolabeled to detect TfR1. Briefly, cells were labeled with a mouse anti-TfR1 (H68.4) primary antibody followed by an anti-mouse AF488 secondary antibody. In FIG. 20B CHO-TRVb cells were transfected with TfR1-CoilE or TfR1 and fixed and permeabilized prior to labeling with VIP E/R and immunolabeling. Cells were treated with CoilR-Cy5, washed and then treated with anti-TfR1. The order of addition did not affect labeling efficiency. Then cells were treated with an anti-mouse-AF488 to detect anti-TfR1 immunolabeling. Cy5 is false-colored magenta and AF488 is false-colored green, with overlapping signal indicated by white in the channel merge.

In FIG. 24 ACHO TRVb cells transfected with TfR1, TfR1-miniE or TfR1-CoilE were labeled with Tf-AF488 (50 µg/mL) and 100 nM CoilR-Cy5 at 4° C. After labeling cells were imaged over time during a 30 min incubation at 37° C. Cells were imaged as confocal slices at 63× magnification. Transferrin-AF488 was false-colored green, CoilR-Cy5 was false-colored magenta, and nuclei were stained with Hoechst and false-colored blue. Individual channels are shown in FIG. 24B (blue, green, magenta) for the 5 minute timepoint. A Pearson's correlation analysis was used to compare fluorescence co-localization of CoilR-Cy5 with Transferrin-AF488. The p values are reported on the image and indicate that TfR1-miniE had better co-localization between Tf and CoilR labeling.

In FIG. 25A U-2 OS cells were transfected with EGFP-TM or CoilZ-EGFP-TM and treated with increasing concentrations of CoilY-AF647. Single, live, green fluorescent cells expressing untagged (left) or tagged (right) EGFP-TM were counted and analyzed for labeling without probe peptide (0 nM) or with CoilY-AF647 (50, 100, 300, 500, 750, or 1000 nM). Values within each histogram indicate the median AF647 fluorescence for each cell population. Data analyzed included between 26,000 and 35,000 live, singlet GFP+ cells. FIG. 25B shows median fluorescence enhancement as a function of CoilY-AF647 concentration.

FIG. 26A shows cells treated with CoilY-AF647. FIG. 26B shows cells treated with CoilZ-AF647. In both 26A and 26B, labeling was only observed upon heterodimer formation with peptide tagged EGFP-TM. The merged images include EGFP (green), AF647 (magenta), and nuclear stain (blue), and the scale bar represents 25 µm.

DETAILED DESCRIPTION

Figure 1:
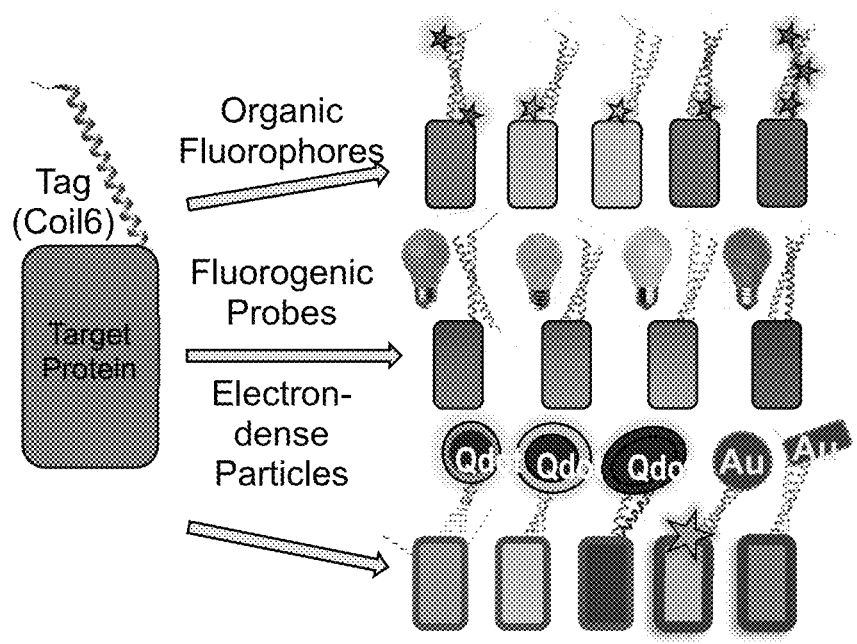
FIG. 1 is a schematic showing the disclosed tag sets with a number of different reporter labels, including organic fluorophores, fluorescent sensors, and nanoparticles.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting. In order to facilitate review of the various embodiments of the disclosure, the following explanations of specific terms are provided:

Antibody: A polypeptide including at least a light chain or heavy chain immunoglobulin variable region which specifically recognizes and binds an epitope of an antigen or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. The VH and VL regions can be further segmented into complementarity determining regions (CDRs) and framework regions. The CDRs (also termed hypervariable regions) are the regions within the VH and VL responsible for antibody binding.

The term "antibody" encompasses intact immunoglobulins, as well the variants and portions thereof, such as Fab fragments, Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker. In dsFvs the chains have been mutated to introduce a disulfide bond to stabilize the association of the chains. The term also includes genetically engineered forms such as chimeric antibodies, heteroconjugate antibodies (such as, bispecific antibodies). See also, Pierce Catalog and Handbook, 1994-1995 (Pierce Chemical Co., Rockford, Ill.); Kuby, J., *Immunology*, 3rd Ed., W.H. Freeman & Co., New York, 1997. The term also includes monoclonal antibodies (all antibody molecules have the same VH and VL sequences and therefore the same binding specificity) and polyclonal antisera (the antibodies vary in VH and VL sequence but all bind a particular antigen such as a tissue antigen.)

An antibody can be used in combination with the disclosed compositions and methods in labeling multiple proteins of interest, including proteins of interest that are expressed on the cell surface.

Contacting: Placement in direct physical association, including contacting of a solid with a solid, a liquid with a liquid, a liquid with a solid, or either a liquid or a solid with a cell or tissue, a protein of interest with a peptide probe, whether in vitro or in vivo. Contacting can occur in vitro with isolated cells or tissue or in vivo by administering to a subject. Contacting can include contacting a liquid (that liquid comprising one or more peptide probes) with a cell comprising a tagged protein of interest.

Fluorescent protein: A protein characterized by a barrel structure that allows the protein to absorb light and emit it at a particular wavelength. Fluorescent proteins include green fluorescent protein (GFP), modified GFPs and GFP derivatives, and other fluorescent proteins, such as CFP, YFP, BFP, mCherry, mEos, mEmerald, ECFP, and circularly permutated fluorescent proteins such as cpVenus.

Label: A label may be any substance capable of aiding a machine, detector, sensor, device, column, or enhanced (for example, through microscopy) or unenhanced human eye from differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism.

Examples of labels include but are not limited to: radioactive isotopes or chelates thereof; dyes (fluorescent or nonfluorescent), sensors, stains, enzymes, nonradioactive metals, such as lanthanides or gold, magnets, protein tags, any antibody epitope, any specific example of any of these; any combination between any of these, or any label now known or yet to be disclosed. A label may be covalently attached to a biomolecule or bound through hydrogen bonding, Van Der Waals or other forces. A label may be covalently or otherwise bound to the N-terminus, the C-terminus or any amino acid of a polypeptide or the 5' end, the 3' end or any nucleic acid residue in the case of a polynucleotide.

One particular example of a label is a small molecule fluorescent dye. Such a label can be conjugated to an antibody such as an antibody that binds a macrophage or CTC marker. One of skill in the art would be able to identify and select any appropriate fluorescent dye or combination of fluorescent dyes for use in the disclosed methods.

Another particular example of a label is an enzyme. In specific examples, the enzyme is conjugated to an antibody that specifically binds an antigen such as a tissue antigen. In still other examples, the enzyme is conjugated to a secondary antibody that specifically binds the antibody that binds the tissue antigen. After an enzyme labeled antibody is bound, a specific substrate for the enzyme is then added to the antibody. In some examples, the activity of the enzyme in the presence of the specific substrate results in a color change that indicates the presence of the label. Such a reaction can be termed a chromogenic reaction. Nonlimiting examples of enzyme labels include horseradish peroxidase, alkaline phosphatase, glucose oxidase, and β-galactosidase.

Another particular example of a label is a protein tag. A protein tag comprises a sequence of one or more amino acids that may be used as a label as discussed above or for use in protein purification. In some examples, the protein tag is covalently bound to the polypeptide. It may be covalently bound to the N-terminal amino acid of a polypeptide, the C-terminal amino acid of a polypeptide or any other amino acid of the polypeptide. Often, the protein tag is encoded by a polynucleotide sequence that is immediately 5' of a nucleic acid sequence coding for the polypeptide such that the protein tag is in the same reading frame as the nucleic acid sequence encoding the polypeptide. Protein tags may be used for all of the same purposes as labels listed above and are well known in the art. Examples of protein tags include chitin binding protein (CBP), maltose binding protein (MBP), glutathione-S-transferase (GST), poly-histidine (His), thioredoxin (TRX), FLAG®, V5, c-Myc, HA-tag, and so forth.

A His-tag facilitates purification and binding to on metal matrices, including nickel or cobalt matrices bound to solid substrates such as agarose plates or beads, glass plates or beads, or polystyrene or other plastic plates or beads. Other protein tags include BCCP, calmodulin, Nus, Thioredoxin, Streptavidin, SBP, and Ty, or any other combination of one or more amino acids that can work as a label described above.

Another particular example of a label is biotin. Biotin is a natural compound that tightly binds proteins such as avidin or streptavidin. A compound labeled with biotin is said to be 'biotinylated'. Biotinylated compounds can be detected with avidin or streptavidin when that avidin or streptavidin is conjugated to another label such as a fluorescent, enzymatic, radioactive or other label. Similarly, a compound can be labeled with avidin or streptavidin and detected with a biotinylated compound.

Another particular example of a label is a quantum dot. Quantum dots are semiconductor crystalline nanospheres which are engineered, inorganic nanocrystals that fluoresce stably and are electron dense. Quantum dots possess a uniform, generally spherical surface area that can be chemically modified to attach biomolecules to them, such as a specific binding agent. Generally, semiconductor nanocrystals can be prepared with relative monodispersity (for example, with the diameter of the core varying approximately less than 10% between semiconductor nanocrystals in the preparation), as has been described previously (Bawendi et al., J. Am. Chem. Soc. 115:8706, 1993). Semiconductor nanocrystals as known in the art have, for example, a core selected from the group consisting of CdSe, CdS, and CdTe (collectively referred to as "CdX"). These semiconductor nanocrystals have been used in place of organic fluorescent dyes as labels in immunoassays (as in U.S. Pat. No. 6,306,610) and as molecular beacons in nucleic acid assays (as in U.S. Pat. No. 6,500,622) among others.

Microscopy: The provided methods can be used with any type of microscopy. For example, the provided protein tags can be used to visualize proteins using light microscopy such as, for example, confocal, widefield, TIRF, and lifetime microscopy; high-resolution light microscopy such as, for example, PALM, STORM, and STED. The provided tags and methods can be used to visualize proteins using electron microscopy such as, CryoEM tomography, TEM, SEM or correlative light and EM (CLEM).

Operably Linked: A promoter or other activating or suppressing nucleic acid sequence is operably linked with a polynucleotide when the promoter is placed in such a way that it has an effect upon the polynucleotide. For instance, a promoter is operably linked to a coding sequence if the promoter affects the transcription or expression of the coding sequence. Operably linked DNA sequences may be contiguous, or they may operate at a distance.

Polynucleotide: a polymer of ribonucleic acid (RNA) or deoxyribonucleic acid (DNA). A nucleic acid is made up of four bases; adenine, cytosine, guanine, and thymine/uracil (uracil is used in RNA). A coding sequence from a nucleic acid is indicative of the sequence of the protein encoded by the nucleic acid. Polynucleotide sequences are generally written with the 5' end on the left and the 3' end on the right.

Polypeptide: Any chain of amino acids, regardless of length or posttranslational modification (such as glycosylation, methylation, ubiquitination, phosphorylation, or the like). Herein as well as in the art, the term 'polypeptide' is used interchangeably with peptide or protein, and is used to refer to a polymer of amino acid residues. The term 'residue' can be used to refer to an amino acid or amino acid mimetic incorporated in a polypeptide by an amide bond or amide bond mimetic. Polypeptide sequences are generally written with the N-terminal amino acid on the left and the C-terminal amino acid to the right of the sequence.

Promoter: A promoter can be any of a number of nucleic acid control sequences that directs transcription of a nucleic acid. Expression by a promoter may be further modulated by enhancer or repressor elements. Numerous examples of promoters are available and well known to those of skill in the art. A nucleic acid comprising a promoter operably linked to a nucleic acid sequence that codes for a particular polypeptide can be termed an expression vector. An expression vector comprising a constitutively active promoter expresses the protein at effectively all times in the cell. A conditionally active promoter directs expression only under certain conditions. For example, a conditionally active promoter might direct expression only in the presence or absence of a particular compound such as a small molecule, amino acid, nutrient, or other compound while a constitutively active promoter directs expression independently of such conditions. Tissue specific promoters (as well as tissue specific enhancers and suppressors) activate or suppress expression in a particular tissue type.

Protein of Interest: A protein of interest is a protein about which information is desired. A protein of interest can be any protein that is or once was part of a living organism. In one example, the information desired is location of the protein of interest on or within a cell, such as a cell in a biological sample that is later subjected to microscopy techniques. In another example, the information desired is the presence or absence of the biomolecule, for example in a sample, such as a biological sample. In another example, the information desired is the presence, absence, and/or location of the target biomolecule in a gel, such as a composite gel. In another example, the information desired is the presence, absence, and/or location of the target biomolecule on a membrane, such as a polyvinylidene fluoride (PVDF) membrane.

Purification: Purification of a polypeptide or molecular complex may be achieved by any method now known or yet to be disclosed. In some examples, purification is achieved by contacting the complex with a reagent that binds to a component of the complex to the exclusion of other components.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide.

Specific binding: An association between two substances or molecules such as the association of a polypeptide with its ligand (for example, the coiled-coil polypeptides disclosed herein). As disclosed here, the polypeptide has specificity for the other member of its pair to the exclusion of other, non-similar polypeptides. Binding can be detected by any procedure known to one skilled in the art, such as by physical or functional properties. Binding can also be detected by visualization of a label conjugated to the polypeptide.

Peptide Probes and Tag Sets

Disclosed herein are peptide probes comprising a polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9, SEQ ID NO:10, SEQ ID NO:11, SEQ ID NO:12, SEQ ID NO:13 or SEQ ID NO:14. The peptide probes further comprise a label. The disclosed peptide probes comprise coiled-coil domains that bind a partner in a binding pair, also referred to herein as a tag set. For example, a peptide probe comprising SEQ ID NO: 1 will bind specifically to another polypeptide comprising SEQ ID NO: 2. A peptide probe comprising SEQ ID NO: 2 will bind specifically to another polypeptide comprising SEQ ID NO: 1. A peptide probe comprising SEQ ID NO: 3 will bind specifically to another polypeptide comprising SEQ ID NO: 4. A peptide probe comprising SEQ ID NO: 4 will bind specifically to another polypeptide comprising SEQ ID NO: 3. a peptide probe comprising SEQ ID NO: 5 will bind specifically to another polypeptide comprising SEQ ID NO: 6. A peptide probe comprising SEQ ID NO: 6 will bind specifically to another polypeptide comprising SEQ ID NO: 5. A peptide probe comprising SEQ ID NO: 7 will bind specifically to another polypeptide comprising SEQ ID NO: 8. A peptide probe comprising SEQ ID NO: 8 will bind specifically to another polypeptide comprising SEQ ID NO: 7. A peptide probe comprising SEQ ID NO:9 will bind specifically to another polypeptide comprising SEQ ID NO:10. The peptide probe can comprise one or more conservative amino acid substitutions, provided that it can still bind its partner in the tag set with about the same affinity as a polypeptide with the original sequence.

The pairs discussed below can be used in a variety of combinations to visualize multiple proteins of interest. Each pair can be used to label two different proteins of interest. For example, a first protein of interest can include SEQ ID NO:7 and a first peptide probe can include SEQ ID NO:8. In the same cell, a second protein of interest can include SEQ ID NO:8 and a second peptide probe can include SEQ ID NO:7. As long as the first and second probes are labeled with distinguishable labels, each pair can advantageously be used to identify two proteins of interest. Each peptide probe can be labeled with one or more labels so proteins can be visualized using multiple platforms. Further, multiple pairs can be used to label multiple proteins. For example, CoilY/Z paid and CoilE/R pair can be used to label up to four proteins, e.g., within a single cell or in vitro.

TABLE 1

Versatile Interacting Peptide Tag Pairs.

| Pair | Peptide | Peptide Sequences |
|---|---|---|
| VIP Y/Z (VIP 5/6) | CoilY (Coil5) | NT VKELKNY IQELEER NAELKNL KEHLKFA KAELEFE LAAHKFE (SEQ ID NO: 7) |
| | CoilZ (Coil6) | QKVAQLKNR VAYKLKE NAKLENI VARLEND NANLEKD IANLEKD IANLERD VAR (SEQ ID NO: 8) |
| VIP 1/2 | Coil1 | NL VAQLENE VASLENE NETLKKK NLHKKDL IAYLEKE IANLRKK IEE (SEQ ID NO: 3) |
| | Coil2 | ARNAYLRKK IARLKKD NLQLERD EQNLEKI IANLRDE IARLENE VASHEQ (SEQ ID NO: 4) |
| VIP 3/4 | Coil3 | NE VTTLEND AAFIENE NAYLEKE IARLRKE KAALRNR LAHKK (SEQ ID NO: 5) |
| | Coil4 | QKVAELKNR VAVKLNR NEQLKNK VEELKNR NAYLKNE LATLENE VARLEN DVAE (SEQ ID NO: 6) |
| VIP E/R (VIPER) | CoilR | LEIR AAFLRQR NTALRTE VAELEQE VQRLENE VSQYETR YGPL (SEQ ID NO: 1) |
| | CoilE | LEIE AAFLERE NTALETR VAELRQR VQRLRNR VSQYRTR YGPL (SEQ ID NO: 2) |
| Mini-VIPER | MiniR | LEIR VAFLRQR NTALRTE VAELEQE VQRLENR YGPL (SEQ ID NO: 9) V: mutation from A to V to improve interface R: mutation from E to R to improve charge balance. Removal of: VSQYETR to shorten tag and improve charge balance. |
| | MiniE | LEIE AAFLERE NTALETR VAELRQR VQRLRNE YGPL (SEQ ID NO: 10) E: Mutation of R to E to improve charge balance. Removal of VSQYRTR to shorten tag and to improve the charge balance. |

Provided are peptide probes comprising a polypeptide of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO:10 and a label. Optionally, the label is selected from a fluorescent small molecule, a fluorescent protein, a quantum dot, a gold nanoparticle, streptavidin, or biotin. Optionally, the peptide probes further comprise a tag selected from glutathione-S-transferase, poly-His, avidin, streptavidin, FLAG, V5, Myc, HA, or NE. Optionally, the label is added post-translationally. Optionally, the peptide probe further comprises a cell penetrating sequence.

Examples of conservative amino acid substitutions are as follows:

| Original Amino Acid | Conservative Substitutions |
|---|---|
| Ala | Ser, Gly |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The peptide probes can further comprise a label. Labels that can be attached to the disclosed protein tags include fluorescent labels (including fluorescent proteins), fluorogenic labels (including pH sensitive and/or enzyme activated fluorogenic labels,) or electron dense labels such as quantum dots or gold. Labels that can be used with the disclosed compositions and methods include quantum dots such as Qdot525, Qdot565, and Qdot655. These quantum dots are all less than 20 nm in size and distinguishable using EM on the basis of size and shape. Additional labels include gold particles with sizes such as 1.5 nm, 5 nm, 10 nm, and 20 nm. Labels can be added post-translationally.

Optionally, the provide probes can include two or more labels. For example, extremely bright probes are useful for super-resolution microscopy. The provided probe peptides can be functionalized to display one or more fluorophores per coil. (FIG. 1). For example, a fluorescent dye can be added in two or more locations along the coil. This results in a brighter signal enabling longer imaging (time-lapse) and better resolution by super-resolution microscopy.

By way of another example, a "fluoronanogold" type approach can be used by placing a fluor at one end and a gold nanoparticle at the other end. Such dual labeled probes can be visualized, for example, by CLEM, the combination of a fluorescence microscope and electron microscope.

Optionally, a pH-insensitive dye and a pH sensitive dye can be placed on the same probe to detect pH changes within cells. A target protein can be tracked at all locations in a cell using a probe peptide comprising the pH insensitive dye and it can be determined when the target protein arrives at an area having a different pH, for example when it hits a late endosome or lysosome, by simultaneously imaging the pH sensitive dye (sensor). In this example, one color is "always on" and the other is environmentally sensitive.

The peptide probes can also comprise a protein tag. These include chitin binding protein, maltose binding protein, glutathione-S-transferase, a poly-His tag, avidin, streptavidin, or a FLAG tag. Other affinity tags include epitope tags such as V5, Myc, HA, NE, and others as well as fluorescent proteins. Protein tags can be used for any of a number of purposes including detection and purification of the peptide probe. A protein tag can be used as both a label and as a purification mechanism as well as for other uses. The peptide probe can also comprise a subcellular localization sequence.

Thus, probe peptides are described that comprise a peptide attached to a reporter, such as an organic fluorophore, a pH-sensitive fluorophore, an enzyme activated fluorophore, a redox-sensitive fluorophore, a fluorogenic probe, a nonfluorescent protein or an electron dense particle. The reporter can be attached to the peptide using a variety of conjugation reactions, including amine reactive probes, such as succinimidyl esters, isothiocyanates, or sulfonyl chlorides, thiol reactive probes, such as maleimides or iodoacetamides, or via "click chemistry". For labeling with click chemistry, a bio-orthogonal reaction, such as a selective azide-alkyne ligation, would be used to attach a reporter to the peptide. In such a case, the azide or alkyne ("click reactive group") could be introduced synthetically or through the addition of an amino acid analogue (unnatural amino acid).

Additional modifications can be made to the disclosed peptide probes. Such modifications can be made to, for example, change the dimer interface or salt bridges, improve labeling dynamics, introduce a reactive moiety, shorten or lengthen the sequence or alter affinities. Formaldehyde fixation of cells can cross-link the coiled coils making binding permanent. Alternatively, a covalent cross-linker (i.e., an unnatural amino acid) can be introduced into a probe peptide.

Difficulties in transfection can be observed that could require alternative delivery strategies such as high efficiency lentiviral vectors. In addition, knock-in cell lines with the VIP-tagged protein expressed under endogenous control can be generated. Additional coiled coil heterodimers can be used in the creation of new tag sets, including the dimer "E3-K3," which are described in Yano et al., *ACS Chem. Biol.* 3(6):341-45 (2008) and peptides described by Reinke et al., JACS 132:6025-31 (2010).

Methods of Visualizing Proteins of Interest

Disclosed are methods of visualizing one or more proteins of interest. Such methods include expressing a tagged protein of interest in a cell. The tagged protein of interest comprises the protein of interest and a tag with a sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9, or SEQ ID NO:10 covalently bound to the protein of interest. The tag can be within the protein, at the N-terminus of the protein of interest or the C-terminus of the protein of interest. For example, the tag can be introduced into the middle of a protein, such as within a flexible loop or after a disordered sequence.

Provided are methods of visualizing a first protein of interest within a cell. The methods include (a) expressing a first tagged protein of interest in the cell comprising the first protein of interest and a first polypeptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9, or SEQ ID NO:10; (b) contacting the first tagged protein of interest with a first peptide probe, said first peptide probe comprising a first label and a second polypeptide selected from SEQ ID NO: 1 if the first tagged protein of interest comprises SEQ ID NO: 2; SEQ ID NO: 2 if the first tagged protein of interest comprises SEQ ID NO: 1; SEQ ID NO: 3 if the first tagged protein of interest comprises SEQ ID NO: 4; SEQ ID NO: 4 if the first tagged protein of interest comprises SEQ ID NO: 3; SEQ ID NO: 5 if the first tagged protein of interest comprises SEQ ID NO: 6; SEQ ID NO: 6 if the first tagged protein of interest comprises SEQ ID NO: 5; SEQ ID NO: 7 if the first tagged protein of interest comprises SEQ ID NO: 8; SEQ ID NO: 8 if the first tagged protein of interest comprises SEQ ID NO: 7; SEQ ID NO:9 if the first tagged protein of interest comprises SEQ ID NO:10; and SEQ ID NO:10 if the first tagged protein of interest comprises SEQ ID NO:9; and (c) visualizing the first label, thereby visualizing the first protein of interest. Optionally, the contacting forms a first tagged protein/peptide probe complex.

The provided methods can be used with any means of visualizing the protein, for example, the provided protein tags can be used to visualize proteins using light microscopy such as, for example, confocal, widefield, TIRF, and lifetime microscopy; high-resolution light microscopy such as, for example, PALM, STORM, and STED. The provided tags and methods can be used to visualize proteins using electron microscopy such as, CryoEM tomography, TEM, SEM or correlative light and EM (CLEM).

Optionally, the provided peptide probes can be used to visualize one or more proteins of interest by providing one or more proteins of interest comprising a first polypeptide tag having SEQ ID NO:1, 2, 3, 4, 5, 6, 7, 8, 9, or 10, contacting the protein of interest with one or more of the appropriate polypeptide probe that binds to the tag on the protein of interest, and visualizing the one or more proteins of interest. Thus, if the protein of interest comprises SEQ ID NO:1 the probe comprises SEQ ID NO:2. As described throughout, the protein pairs can be used together to simultaneously visualize multiple proteins as long as the peptide probes comprise distinguishable labels. For example, the tagged proteins can be resolved on a gel and visualized using the peptide probes. As described in example 12 and FIGS. 5, 10 and 23, these methods are more sensitive than immunoblots and are useful when high specificity antibodies are lacking.

Optionally, the tagged protein of interest or the first peptide probe further comprises a cellular localization peptide. Optionally, the cellular localization peptide targets the tagged protein of interest to the cell surface. Optionally, the first tagged protein of interest further comprises a purification tag. Optionally, the purification tag comprises a His-tag. Optionally, the method further includes purifying the first tagged protein of interest.

Optionally, the first label comprises an organic fluorophore, a pH-sensitive fluorophore, an enzyme activated fluorophore, a redox-sensitive fluorophore, a fluorogenic probe, a nonfluorescent protein or an electron dense particle. Optionally, the first label comprises a fluorescent small molecule, a fluorescent protein, a quantum dot, a gold nanoparticle, biotin, or streptavidin. Optionally, expressing the first tagged protein of interest occurs within a bacterial or mammalian cell. Optionally, expressing the first tagged protein of interest occurs within a transgenic mouse. Optionally, visualizing the first tagged protein complexed with the first labeled peptide probe is performed using microscopy, such as fluorescence microscopy, electron microscopy, or correlative light and electron microscopy.

Optionally, the method further includes visualizing a second protein of interest. Optionally, visualizing the second protein of interest comprises immunolabeling or expression of the second protein of interest in conjunction with a protein tag=. Versatile interacting peptide tags can be imaged in cells that are labeled by immunolabeling, fluorescent protein fusions, SNAP, CLIP, Halo, or other genetic tags. VIP tags are also compatible with small molecule stains, such as a nuclear stain (DAPI) or an organelle marker, such as Mitotracker.

Optionally, two target proteins can be visualized. Visualizing the second protein of interest comprises expressing a second tagged protein of interest comprising the second protein of interest and a second polypeptide selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9, or SEQ ID NO:10; contacting the second tagged protein of interest with a second peptide probe comprising a second label and a second polypeptide selected from SEQ ID NO: 1 if the second tagged protein of interest comprises SEQ ID NO: 2; SEQ ID NO: 2 if the second tagged protein of interest comprises SEQ ID NO: 1; SEQ ID NO: 3 if the second tagged protein of interest comprises SEQ ID NO: 4; SEQ ID NO: 4 if the second tagged protein of interest comprises SEQ ID NO: 3; SEQ ID NO: 5 if the second tagged protein of interest comprises SEQ ID NO: 6; SEQ ID NO: 6 if the second tagged protein of interest comprises SEQ ID NO: 5; SEQ ID NO: 7 if the second tagged protein of interest comprises SEQ ID NO: 8; SEQ ID NO: 8 if the second tagged protein of interest comprises SEQ ID NO: 7; SEQ ID NO:9 if the second tagged protein of interest comprises SEQ ID NO:10; or SEQ ID NO:10 if the second tagged protein of interest comprises SEQ ID NO:9; and visualizing the second label, thereby visualizing the second protein of interest; provided that the first label and the second label are distinguishable from one another.

As discussed throughout, each pair of tags can be used to visualize two proteins so if a first protein of interest comprises SEQ ID NO:1 the peptide probe comprises SEQ ID NO:2 and a second protein of interest comprises SEQ ID NO:2 and the second peptide probe comprises SEQ ID NO:1 as long as the labels on the first and second peptide probes are distinguishable. The provided methods can be used to visualize multiple proteins using multiple VIP tags. Thus, two or more VIP tags can label four or more proteins of interest as long as the labels on the peptide probes are distinguishable. Thus, for example, a first protein of interest can comprise SEQ ID NO:1, a first peptide probe comprises SEQ ID NO:2, a second protein of interest comprises SEQ ID NO:2, a second peptide probe comprises SEQ ID NO:1, a third protein of interest comprises SEQ ID NO:9, a third peptide probe comprises SEQ ID NO:10, and a fourth protein of interest comprises SEQ ID NO:10 and a fourth peptide probe comprises SEQ ID NO:9. The labels of the four different peptide probes can be distinguishable. Optionally, the method further includes visualizing a third, fourth, fifth, or more proteins of interest. The VIP tags are designed as self-sorting pairs that can be used together to image multiple target proteins in cells.

Optionally, the second tagged protein of interest or the second peptide probe further comprises a cellular localization peptide. Optionally, the cellular localization peptide targets the second tagged protein of interest to the cell surface. Optionally, the second label comprises a fluorescent small molecule, a fluorescent protein, a quantum dot, a gold nanoparticle, biotin, or streptavidin. Optionally, the second tagged protein of interest further comprises a purification tag. Optionally, the purification tag comprises a His-tag. Optionally, the method further includes purifying the second tagged protein of interest. Optionally, expressing the second tagged protein of interest occurs within a bacterial or mammalian cell. Optionally, expressing the second tagged protein of interest occurs within a transgenic mouse. Optionally, visualizing the second label is performed using microscopy, such as fluorescence microscopy, electron microscopy, or correlative light and electron microscopy.

Provided herein are expression vectors comprising a first polynucleotide that encodes a first polypeptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO:9 or SEQ ID NO:10; a promoter operably linked to the first polynucleotide. Optionally, the expression vectors also include a second polynucleotide that encodes a second polypeptide that aids in the selection of a cell that is positive for the expression vector, e.g., a selection marker. Optionally, the expression vectors further include a third polynucleotide that encodes a protein of interest operably linked to the first polynucleotide. Optionally, the expression vectors further include a purification tag comprising a His-tag. Optionally, the protein label comprises a fluorescent protein or streptavidin. Optionally, the expression vectors further include a multiple cloning site for easy insertion of other polynucleotide sequences. Optionally, the fourth polynucleotide further encodes a peptide probe. Optionally, the promoter is a tissue specific promoter. Optionally, the expression vectors further include one or more regulators of expression that limit expression to one or more particular cells or tissues. Optionally, the expression vectors further include a transcriptional enhancer, a transcriptional suppressor, or a microRNA recognition element.

The tagged protein of interest can be expressed within the cell by any of a number of methods known in the art. A nucleic acid expression vector configured to express the tagged protein of interest can be stably or transiently transfected into the cell. The expression vector can comprise a promoter operably linked to a polynucleotide encoding the tagged protein of interest. The expression vector can also comprise any of a number of other elements including polynucleotides that encode proteins that aid in the identification of cells actively expressing the protein of interest (such as selective markers) and polynucleotides that restrict the expression of the tagged protein of interest to particular cell types or conditions such as enhancer elements, suppressor elements, microRNA recognition elements, and the like. One skilled in the art in light of this disclosure can produce an appropriate expression vector for use in experiments involving any protein of interest. The tagged protein of interest can also comprise any of the protein tags and/or subcellular localization sequences described for peptide probes above.

The methods further involve contacting the tagged protein of interest with a peptide probe as described throughout. Visualization of the label conjugated to the peptide probe results in visualization of the protein of interest. The contacting can occur in vitro, within a cell, such as a human or other mammalian cell or in vivo, such as within a transgenic rodent. For example, a transgenic mouse can be made that expresses the tagged protein of interest, such as within a particular cell type. Then the corresponding peptide probe to the tag on the tagged protein of interest can be administered to the mouse, appropriate tissue samples removed from the mouse, and the label from the peptide probe visualized. Visualization can be performed by any of a number of methods such as by fluorescence microscopy, flow cytometry, electron microscopy, correlative light electron microscopy, or any other method that facilitates the visualization of labels within cells. In light of this disclosure, one skilled in the art will understand how to select the proper label for a given visualization method.

As noted throughout, the disclosed tag sets specifically bind one another, multiple tag sets can be used in a single cell. A tag set with a tag of SEQ ID NO: 1 conjugated to the protein of interest and a peptide probe of SEQ ID NO: 2 can be used in combination with a tag set with a tag of SEQ ID NO: 2 conjugated to the protein of interest and a peptide probe of SEQ ID NO: 1, provided that the label on the peptide probe of SEQ ID NO: 2 is distinguishable from the label on the peptide probe of SEQ ID NO: 1. Similarly, a tag set with a tag of SEQ ID NO: 1 conjugated to the protein of interest and a peptide probe of SEQ ID NO: 2 can be used in combination with a tag set with a tag of SEQ ID NO: 3 conjugated to the protein of interest and a peptide probe of SEQ ID NO: 4, provided that the label on the peptide probe of SEQ ID NO: 2 is distinguishable from the label on the peptide probe of SEQ ID NO: 4. Any number of the disclosed tag sets can be used in any combination with one another, with other tag sets comprising coiled-coil motifs, or with other labeling methods such as stains or immunolabeling methods using antibodies. In light of this disclosure, one skilled in the art can select the probe sets, labels, and other labeling methods to combine with a particular visualization method to visualize a plurality of proteins of interest within a cell.

Kits

Disclosed herein are kits that comprise one or more expression vectors configured to express one or more tagged proteins of interest in and/or one or more peptide probes. An appropriate amount of expression vector or peptide probe, label, as well as other reagents for use in the detection and visualization of proteins of interest in a cell, the cloning of nucleic acid sequences into expression vectors, the transfection of an expression vector into a cell, or the conjugation of a label to a peptide probe can be provided.

The components of the kit can be provided in any physical form, such as an aqueous solution or a freeze dried or lyophilized powder. The components can be provided in any conventional container appropriate for holding the particular component. These include but need not be limited to microfuge tubes, ampules, or bottles. The kit can also include equipment, other reagents, or instructions useful in detecting one or more proteins of interest. The kit can also include software configured to make a computing device to perform acts of the various methods described herein.

Provided herein are kits comprising a peptide probe comprising SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or any combination thereof and instructions for use. Optionally, the kits comprise peptide probes comprising SEQ ID NO:1, SEQ ID NO:2, SEQ ID NO:9 and SEQ ID NO:10. Optionally, the kits comprise peptide probes comprising SEQ ID NO:1, SEQ ID NO:2, SEQ ID NO:7, and SEQ ID NO:8. Optionally, the peptide probes in the kits include one or more labels. The labels can be attached to the peptide probes or provided in a separate container. Optionally, the kits further comprise one or more expression vectors configured to express a protein of interest with a polypeptide tag having SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, as appropriate. For example, if the kit includes a peptide probe comprising SEQ ID NO:9, an expression vector will comprise SEQ ID NO:10. Similarly, if the kit includes a peptide probe having SEQ ID NO:1, the expression vector will comprise SEQ ID NO:2.

Thus, provided herein are kits comprising a first expression vector and a first peptide probe, provided that if the first expression vector comprises a polynucleotide encoding SEQ ID NO: 1, the first peptide probe comprises a polypeptide of SEQ ID NO: 2; if the first expression vector comprises a polynucleotide encoding SEQ ID NO: 2, the first peptide probe comprises a polypeptide of SEQ ID NO: 1; if the first expression vector comprises a polynucleotide encoding SEQ ID NO: 3, the first peptide probe comprises a polypeptide of SEQ ID NO: 4; if the first expression vector comprises a polynucleotide encoding SEQ ID NO: 4, the first peptide probe comprises a polypeptide of SEQ ID NO: 3; if the first expression vector comprises a polynucleotide encoding SEQ ID NO: 5, the first peptide probe comprises a polypeptide of SEQ ID NO: 6; if the first expression vector comprises a polynucleotide encoding SEQ ID NO: 6, the first peptide probe comprises a polypeptide of SEQ ID NO: 5; if the first expression vector comprises a polynucleotide encoding SEQ ID NO: 7, the first peptide probe comprises a polypeptide of SEQ ID NO: 8; if the first expression vector comprises a polynucleotide encoding SEQ ID NO: 8, the first peptide probe comprises a polypeptide of SEQ ID NO: 7; if the first expression vector comprises a polynucleotide encoding SEQ ID NO:9, the first peptide probe comprises a polypeptide of SEQ ID NO:10; and if the first expression vector comprises a polynucleotide encoding SEQ ID NO:10, the first peptide probe comprises a polypeptide of SEQ ID NO:9. The kits can include multiple probes and/or multiple expression vectors.

Optionally, the kit further comprises a label and a post-translational labeling reagent that conjugates the label to the peptide probe. Optionally, the label is selected from a fluorescent small molecule, a quantum dot, a gold nanoparticle, biotin, or streptavidin. Optionally, the kit further comprises a transfection reagent.

A kit could include a set of probe peptides, with each probe peptide sample labeled with a distinct reporter. For example, the kit might include CoilR conjugated to one or more various fluorophores, such as CoilR-coumarin, CoilR-fluorescein, CoilR-Cy5, and CoilR-Cy7, electron dense particles, such as CoilR-Q-dots and CoilR-gold particles of different sizes/shapes, or combinations thereof.

Optionally, the kits further comprise one or more additional expression vectors and/or one or more additional peptide probes. For example, the kits can include a second expression vector and a second peptide probe. Optionally, the kits include a third expression vector and a third peptide probe. Optionally, the kits include a fourth expression vector and a fourth peptide probe. Optionally, the kits include a fifth expression vector and a fifth peptide probe. Optionally, if the first expression vector comprises a polynucleotide encoding SEQ ID NO: 1 and the first peptide probe comprises a polypeptide of SEQ ID NO: 2, the second expression vector will comprise polynucleotide encoding SEQ ID NO: 2, and the second peptide probe comprises a polypeptide of SEQ ID NO: 1. Optionally, the first expression vector comprises a polynucleotide encoding SEQ ID NO: 1, if the first peptide probe comprises a polypeptide of SEQ ID NO: 2, the second expression vector will comprise a polynucleotide encoding SEQ ID NO: 3, and the second peptide probe comprises a polypeptide of SEQ ID NO: 4. Optionally, if the first expression vector comprises a polynucleotide encoding SEQ ID NO: 2 and the first peptide probe comprises a polypeptide of SEQ ID NO: 1, the second expression vector will comprise a polynucleotide encoding SEQ ID NO: 3, and the second peptide probe comprises a polypeptide of SEQ ID NO: 4. Optionally, the first expression vector comprises a polynucleotide encoding SEQ ID NO: 2, the first peptide probe comprises a polypeptide of SEQ ID NO: 1, the second expression vector comprises a polynucleotide encoding SEQ ID NO: 4, and the second peptide probe comprises a polypeptide of SEQ ID NO: 3. Optionally, the first expression vector comprises a polynucleotide encoding SEQ ID NO: 1, the first peptide probe comprises a polypeptide of SEQ ID NO: 2, the second expression vector comprises a polynucleotide encoding SEQ ID NO: 5, and the second peptide probe comprises a polypeptide of SEQ ID NO: 6. Optionally, the first expression vector comprises a polynucleotide encoding SEQ ID NO: 1, the first peptide probe comprises a polypeptide of SEQ ID NO: 2, the second expression vector comprises a polynucleotide encoding SEQ ID NO: 6, and the second peptide probe comprises a polypeptide of SEQ ID NO: 5. Optionally, the first expression vector comprises a polynucleotide encoding SEQ ID NO: 2, the first peptide probe comprises a polypeptide of SEQ ID NO: 1, the second expression vector comprises a polynucleotide encoding SEQ ID NO: 5, and the second peptide probe comprises a polypeptide of SEQ ID NO: 6. Optionally, the first expression vector comprises a polynucleotide encoding SEQ ID NO: 2, the first peptide probe comprises a polypeptide of SEQ ID NO: 1, the second expression vector comprises a polynucleotide encoding SEQ ID NO: 6, and the second peptide probe comprises a polypeptide of SEQ ID NO: 5. Optionally, the first expression vector comprises a polynucleotide encoding SEQ ID NO: 1, the first peptide probe comprises a polypeptide of SEQ ID NO: 2, the second expression vector comprises a polynucleotide encoding SEQ ID NO: 7, and the second peptide probe comprises a polypeptide of SEQ ID NO: 8. Optionally, the first expression vector comprises a polynucleotide encoding SEQ ID NO: 1, the first peptide probe comprises a polypeptide of SEQ ID NO: 2, the second expression vector comprises a polynucleotide encoding SEQ ID NO: 8, and the second peptide probe comprises a polypeptide of SEQ ID NO: 7. Optionally, the first expression vector comprises a polynucleotide encoding SEQ ID NO: 2, the first peptide probe comprises a polypeptide of SEQ ID NO: 1, the second expression vector comprises a polynucleotide encoding SEQ ID NO: 7, and the second peptide probe comprises a polypeptide of SEQ ID NO: 8. Optionally, the first expression vector comprises a polynucleotide encoding SEQ ID NO: 2, the first peptide probe comprises a polypeptide of SEQ ID NO: 1, the second expression vector comprises a polynucleotide encoding SEQ ID NO: 8, and the second peptide probe comprises a polypeptide of SEQ ID NO: 7. Optionally, the first expression vector comprises a polynucleotide encoding SEQ ID NO: 3, the first peptide probe comprises a polypeptide of SEQ ID NO: 4, the second expression vector comprises a polynucleotide encoding SEQ ID NO: 5, and the second peptide probe comprises a polypeptide of SEQ ID NO: 6. Optionally, the first expression vector comprises a polynucleotide encoding SEQ ID NO: 3, the first peptide probe comprises a polypeptide of SEQ ID NO: 4, the second expression vector comprises a polynucleotide encoding SEQ ID NO: 6, and the second peptide probe comprises a polypeptide of SEQ ID NO: 5. Optionally, the first expression vector comprises a polynucleotide encoding SEQ ID NO: 4, the first peptide probe comprises a polypeptide of SEQ ID NO: 3, the second expression vector comprises a polynucleotide encoding SEQ ID NO: 5, and the second peptide probe comprises a polypeptide of SEQ ID NO: 6. Optionally, the first expression vector comprises a polynucleotide encoding SEQ ID NO: 4, the first peptide probe comprises a polypeptide of SEQ ID NO: 3, the second expression vector comprises a polynucleotide encoding SEQ ID NO: 6, and the second peptide probe comprises a polypeptide of SEQ ID NO: 5. Optionally, the first expression vector comprises a polynucleotide encoding SEQ ID NO: 3 the first peptide probe comprises a polypeptide of SEQ ID NO: 4, the second expression vector comprises a polynucleotide encoding SEQ ID NO: 7, and the second peptide probe comprises a polypeptide of SEQ ID NO: 8. Optionally, the first expression vector comprises a polynucleotide encoding SEQ ID NO: 3, the first peptide probe comprises a polypeptide of SEQ ID NO: 4, the second expression vector comprises a polynucleotide encoding SEQ ID NO: 8, and the second peptide probe comprises a polypeptide of SEQ ID NO: 7. Optionally, the first expression vector comprises a polynucleotide encoding SEQ ID NO: 4, the first peptide probe comprises a polypeptide of SEQ ID NO: 3, the second expression vector comprises a polynucleotide encoding SEQ ID NO: 7, and the second peptide probe comprises a polypeptide of SEQ ID NO: 8. Optionally, the first expression vector comprises a polynucleotide encoding SEQ ID NO: 4, the first peptide probe comprises a polypeptide of SEQ ID NO: 3, the second expression vector comprises a polynucleotide encoding SEQ ID NO: 8, and the second peptide probe comprises a polypeptide of SEQ ID NO: 7. Optionally, the first expression vector comprises a polynucleotide encoding SEQ ID NO: 5, the first peptide probe comprises a polypeptide of SEQ ID NO: 6, the second expression vector comprises a polynucleotide encoding SEQ ID NO: 7, and the second peptide probe comprises a polypeptide of SEQ ID NO: 8. Optionally, the first expression vector comprises a polynucleotide encoding SEQ ID NO: 5, the first peptide probe comprises a polypeptide of SEQ ID NO: 6, the second expression vector comprises a polynucleotide encoding SEQ ID NO: 8, and the second peptide probe comprises a polypeptide of SEQ ID NO: 7. Optionally, the first expression vector comprises a polynucleotide encoding SEQ ID NO: 6, the first peptide probe comprises a polypeptide of SEQ ID NO: 5, the second expression vector comprises a polynucleotide encoding SEQ ID NO: 7, and the second peptide probe comprises a polypeptide of SEQ ID NO: 8. Optionally, the first expression vector comprises a polynucleotide encoding SEQ ID NO: 6, the first peptide probe comprises a polypeptide of SEQ ID NO: 5, the second expression vector comprises a polynucleotide encoding SEQ ID NO: 8, and the second peptide probe comprises a polypeptide of SEQ ID NO: 7. Optionally, the first expression vector comprises a polynucleotide encoding SEQ ID NO: 3, the first peptide probe comprises a polypeptide of SEQ ID NO: 4, the second expression vector comprises a polynucleotide encoding SEQ ID NO: 4, and the second peptide probe comprises a polypeptide of SEQ ID NO: 3. Optionally, the first expression vector comprises a polynucleotide encoding SEQ ID NO: 5, the first peptide probe comprises a polypeptide of SEQ ID NO: 6, the second expression vector comprises a polynucleotide encoding SEQ ID NO: 6, and the second peptide probe comprises a polypeptide of SEQ ID NO: 5. Optionally, the first expression vector comprises a polynucleotide encoding SEQ ID NO: 7, the first peptide probe comprises a polypeptide of SEQ ID NO: 8, the second expression vector comprises a polynucleotide encoding SEQ ID NO: 8, and the second peptide probe comprises a polypeptide of SEQ ID NO: 7.

EXAMPLES

The following examples are for illustration only. In light of this disclosure, those skilled in the art will recognize that variations of these examples and other examples of the disclosed invention be possible without undue experimentation.

Example 1—VIP E/R, VIP V/Z, and Other Tag Sets

Fluorescent proteins (FPs) are useful protein tags for confocal fluorescence microscopy. Yet, FPs are large (~30 kDa), and FP fusions can disrupt protein function, trafficking, stability, and sub-cellular morphology. There are some protein tags compatible with organic fluorophores, which offer better spectral properties compared to the FP chromophores. These protein tags include fusions to DNA alkyl transferases (SNAP and CLIP tags), a dehalogenase (Halo tag), a dihydrofolate reductase (TMP tag), or antibody fragments (fluorogen-activating proteins, or FAPs). Each of these tags enables fluorophores to be targeted to a protein, but the substantial tag sizes (>18 kDa) offer only a modest improvement over FP fusions. A few short peptide tags have been described, but they tend to bind non-specifically to other moieties (e.g., tetracysteine and biotin ligase tag) and provide a limited number color choices. All of these protein and peptide tags were designed for tracking one target at a time. Among these tags only the SNAP tag has been modified to enable two-color imaging (e.g., SNAP/CLIP). Without extensive re-engineering, none of these tags are ideal for tracking multi-protein interactions by light and EM.

Alternative strategies have utilized genetically-encoded tetracysteine motifs or poly-histidine Ni-binding systems, for example, but these suffer from other drawbacks such as high toxicity and off-target reactivity. Genetically-encoded aldehyde tags have been described, however this strategy is not generally compatible with live cells and is not feasible for use with multi-color imaging.

The disclosed polypeptide tags comprising a coiled-coil motif overcome these limitations. First, the coiled-coil motif has been characterized in many studies and α-helical peptides (coils) are simple structures that are amenable to covalent modifications. The internal positions of the helix-helix face are non-polar, facilitating a strong hydrophobic interaction between the two coils. Acidic or basic residues are found in the positions flanking the hydrophobic core and strengthen and orient the binding through electrostatic pairing and salt-bridging. Coiled-coiled peptides can be genetically altered to favor heterodimer formation, not interact with other coiled-coil pairs, and posses sub-nanomolar dissociation constants. Due to their small size, (<8 kDa per coil) the disclosed polypeptide tags are less likely than large protein fusions (>18 kDa) to disrupt protein catalytic activity, binding interactions, or trafficking. Additionally, the small tag places the label nearer to the protein of interest than, for example, antibodies which can improve image resolution.

A set of heterodimeric polypeptide tag pairs were selected to be used in an initial study. These coiled-coiled pairs were selected because they will self-sort into specific heterodimer pairs, which means that different pairs can be used in tandem to label multiple proteins at once. These polypeptide tag pairs are small, biocompatible, and dimerize with high affinity (Table 2).

TABLE 2

Sequences and properties of peptide coils and VIP tags.

| Pair | Peptide | Peptide Sequences | MW | pI | $K_D$ |
|---|---|---|---|---|---|
| VIP Y/Z (VIP 5/6) | CoilY (Coil5) | NT VKELKNY IQELEER NAELKNL KEHLKFA KAELEFE LAAHKFE (SEQ ID NO: 7) | 5.29 | 5.6 | <15 nM |
| | CoilZ (Coil6) | QKVAQLKNR VAYKLKE NAKLENI VARLEND NANLEKD IANLEKD IANLERD VAR (SEQ ID NO: 8) | 6.20 | 8.3 | |
| VIP 1/2 | Coil1 | NL VAQLENE VASLENE NETLKKK NLHKKDL IAYLEKE IANLRKK IEE (SEQ ID NO: 3) | 5.51 | 5.8 | <10 nM |
| | Coil2 | ARNAYLRKK IARLKKD NLQLERD EQNLEKI IANLRDE IARLENE VASHEQ (SEQ ID NO: 4) | 5.96 | 8.4 | |
| VIP 3/4 | Coil3 | NE VTTLEND AAFIENE NAYLEKE IARLRKE KAALRNR LAHKK (SEQ ID NO: 5) | 4.91 | 8.3 | <30 nM |
| | Coil4 | QKVAELKNR VAVKLNR NEQLKNK VEELKNR NAYLKNE LATLENE VARLEN DVAE (SEQ ID NO: 6) | 6.29 | 8.3 | |
| VIP E/R (VIPER) | CoilR | LEIR AAFLRQR NTALRTE VAELEQE VQRLENE VSQYETR YGPL (SEQ ID NO: 1) | 5.12 | 4.9 | <2 pM |
| | CoilE | LEIE AAFLERE NTALETR VAELRQR VQRLRNR VSQYRTR YGPL (SEQ ID NO: 2) | 5.20 | 10.6 | |
| Mini-VIPER | MiniR | LEIR VAFLRQR NTALRTE VAELEQE VQRLENR YGPL (SEQ ID NO: 9) V: mutation from A to V to improve interface R: mutation from E to R to improve charge balance. Removal of: VSQYETR to shorten tag and improve charge balance. | 4.31 | 6.4 | Na |

TABLE 2-continued

Sequences and properties of peptide coils and VIP tags.

| Pair | Peptide | Peptide Sequences | MW | pI | $K_D$ |
|---|---|---|---|---|---|
| | MiniE | LEIE AAFLERE NTALETR VAELRQR VQRLRNE YGPL (SEQ ID NO: 10)<br>E: Mutation of R to E to improve charge balance.<br>Removal of VSQYRTR to shorten tag and to improve the charge balance. | 4.28 | 5.2 | |

CoilR and CoilE (SEQ ID NO: 1 and SEQ ID NO: 2) were adapted to create the VIP E/R tag set. Binding between these two polypeptides was shown to be nearly irreversible ($K_D$~$10^{-11}$M) even in the presence of elevated temperatures or denaturants. Another three heterodimerizing pairs (SEQ ID NOs: 3-8) were also selected. These six peptides (Coils 1-6) were reported to self-sort into precisely matched pairs, suggesting that the three pairs could be used together for multi-protein labeling without "cross-talk". All of the disclosed tags disfavor homodimerization and are designed to be cell compatible. These are good features for tracking multiple cellular proteins simultaneously.

The tags CoilY and CoilZ were derived from the peptides SYNZIP5 and ZYNZIP6. As reported by Reinke and coworkers, homodimerization of these two peptides is disfavored, and they do not cross react with common human leucine zippers (e.g., BATF, FOS, ATF4). SYNZIP5:SYNZIP6 forms a tight heterodimeric interaction ($K_D$<15 nM) with a reasonable melting temperature ($T_m$=32° C.). To generate CoilY and CoilZ, gene assembly PCR was used and recombinant expression of the tags in E. coli. A histidine tag was included for affinity purification and a cysteine was included for maleimide-fluorophore conjugation (optionally a lysine can be used). Each peptide was expressed and purified using affinity column chromatography.

The solution phase structures of CoilY and CoilZ were analyzed by circular dichroism spectroscopy (CD) and both peptides found to have α-helical structures. A mixture of the two peptides indicated a coiled-coil structure. Size-exclusion chromatography confirmed heterodimer formation.

To validate the use of the Coil Y/Z pair, fluorophore-conjugated probe peptides and peptide tagged proteins of interest were generated. The probe peptides were prepared via thiol alkylation using fluorescent maleimide conjugates (for example, green fluorescent CoilZ-fluorescein and red fluorescent CoilY-rhodamine). The tagged fluorescent proteins were constructed by fusing the CoilY gene to membrane-targeted constructs. CoilY was fused to the N-terminus of a mCherry construct (CoilY-mCherry-pDisplay) and CoilZ was fused to the N-terminus of enhanced GFP (CoilZ-EGFP-pDisplay)

The CoilY and CoilZ pair could be used to label two protein targets simultaneously. Transfected HEK293FT cell lysates from cells expressing mCherry, CoilY-mCherry, EGFP, or CoilZ-EGFP were resolved by SDS-PAGE and transferred to a PVDF membrane. The membrane was incubated sequentially with CoilZ-fluorescein and CoilY-rhodamine before imaging. GFP and mCherry fluorescence was not preserved due to SDS-PAGE protein denaturation. However, specific coiled-coil heterodimer formation could be detected for both CoilY-mCherry (with CoilZ-fluorescein) and CoilZ-EGFP (with CoilY-rhodamine). The results indicate that use of the CoilY-CoilZ tag set resulted in specific and selective labelling of two distinct targets.

Figure 11:
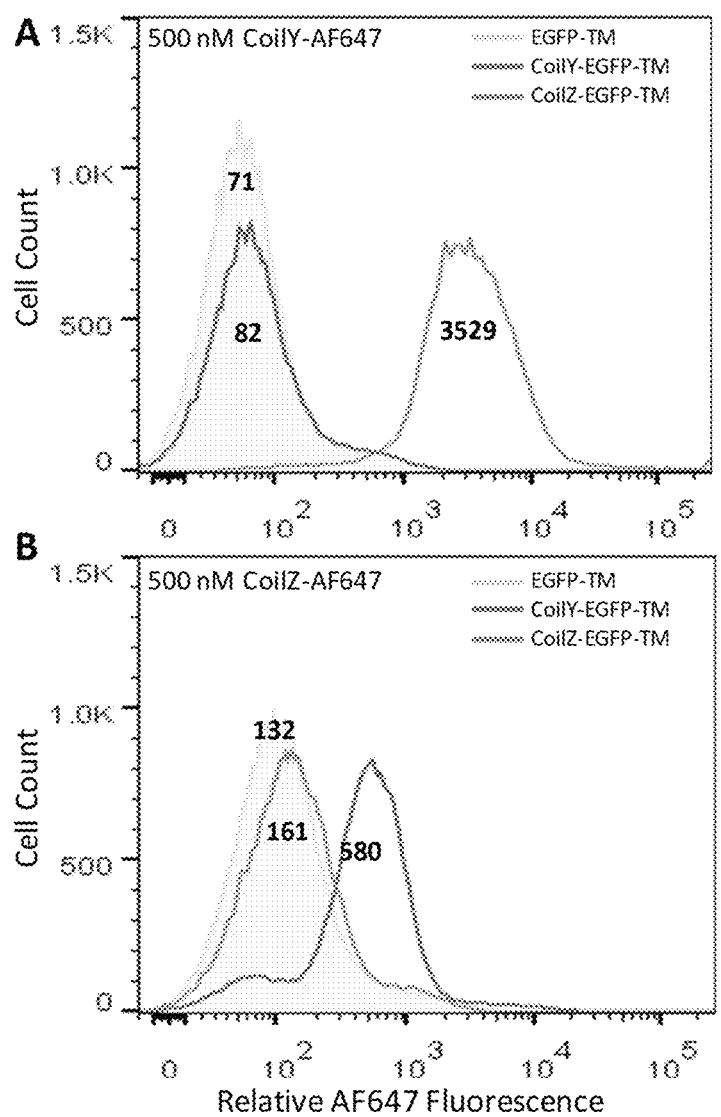
FIG. 11 shows histograms of AF647 fluorescence from flow cytometry. Cells were gated for green fluorescence and analyzed for labeling with CoilY-AF647 (A) or CoilZ-AF647 (B). Transfected cells expressed CoilZ-EGFP-TM (green), CoilY-EGFP-TM (blue), or untagged EGFP-TM (gray). Values in bold indicate the median AF647 fluorescence for each cell population.

The in vitro results were translated to living cells. Flow cytometry was used to evaluate protein labeling in live human osteosarcoma (U-2 OS) cells expressing CoilZ-EGFP-TM, CoilY-EGFP-TM, or untagged EGFP-TM (FIG. 11). Cells were treated with 500 nM AF647-conjugated probe peptide before analysis, and we gated for EGFP-expressing cells. We found that both peptide tags, CoilY and CoilZ, enabled selective protein labeling via heterodimerization. Treatment of cells expressing CoilZ-EGFP-TM with CoilY-AF647 resulted in bright, selective protein labeling with a greater than 40-fold enhancement. Non-specific labeling of untagged EGFP-TM and homodimerization with CoilY-EGFP-TM were minimal for cells exposed to CoilY-AF647. Cells expressing CoilY-EGFP-TM were labeled with CoilZ-AF647, but with only a 4-fold enhancement. Non-specific labeling was slightly higher for cells treated with CoilZ-AF647, and we suspect that this positively charged probe might interact with the negatively charged cell surface resulting in a higher non-specific signal.

Figure 25:
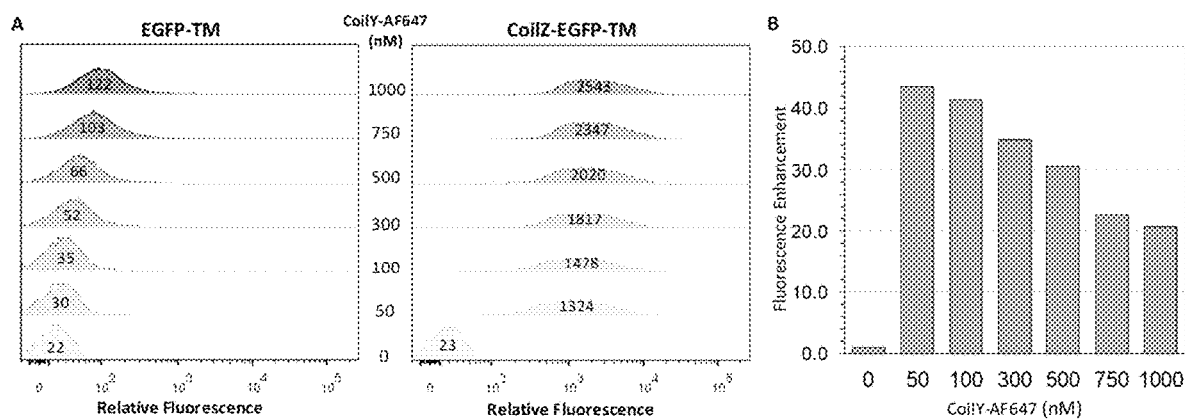
FIGS. 25A and 25B provide flow analysis of cells treated with CoilY-AF647.

Protein labeling was assessed as a function of CoilY-AF647 concentration (FIG. 25). Live cells expressing CoilZ-EGFP-TM or untagged EGFP-TM were treated with a range of CoilY-AF647 concentrations (50 nM to 1000 nM for 30 min at room temperature). Flow cytometry showed that the median AF647 signal increased with increasing concentration of probe peptide. Cells had 21- to 44-fold higher median fluorescence compared to cells expressing untagged protein. Treatment with 300 nM AF647-CoilY gave optimal labeling, with 98% of cells labeled and a 35-fold increase in AF647 fluorescence. Treatment with an excess of probe peptide (i.e., 1000 nM) enhanced the AF647 signal, but at the cost of a small increase in non-specific labeling. These results demonstrate that a range of concentrations could be used successfully to label tagged proteins.

Example 2—VIP E/R and VIP Y/Z are New Tags for Imaging Proteins

Initial experiments validated both VIP E/R (which used CoilR and CoilE) and VIP Y/Z (which used CoilY and CoilZ). Gene assembly PCR was used to generate an expression vector that allowed expression of the polypeptides above. A histidine tag was engineered into each polypeptide to facilitate affinity purification of each peptide on a nickel column and a lysine was engineered into CoilR and/or a cysteine engineered into CoilR, CoilZ, and CoilY to facilitate conjugation of a label to these peptides.

The purified peptides were covalently attached to various fluorophores for subsequent applications. In some examples, the coils were site-specifically biotinylated for subsequent detection by streptavidin-gold or streptavidin-Qdot. These labeled, purified peptides, which are not covalently-conjugated to a protein of interest, are referred to herein as probe peptides. Circular dichroism (CD), size-exclusion chromatography, protein gel electrophoresis, absorption and fluorescence measurements, and interferometry were used to characterize CoilY and CoilZ. It was thus determined that this pair forms an α-helical heterodimer with high affinity. The measured $K_D$ of the binding between CoilZ and CoilY was 3.6 nM.

Figure 3A:
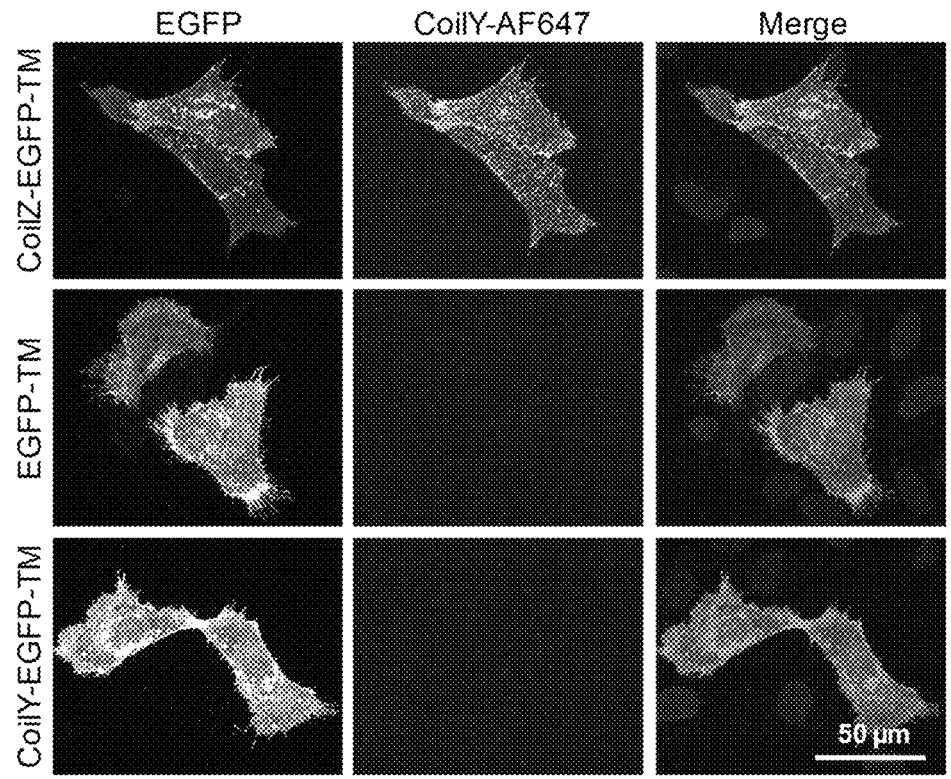
FIG. 3A is a set of images showing CoilZ-GFP binding to CoilY-AF647.
Figure 3B:
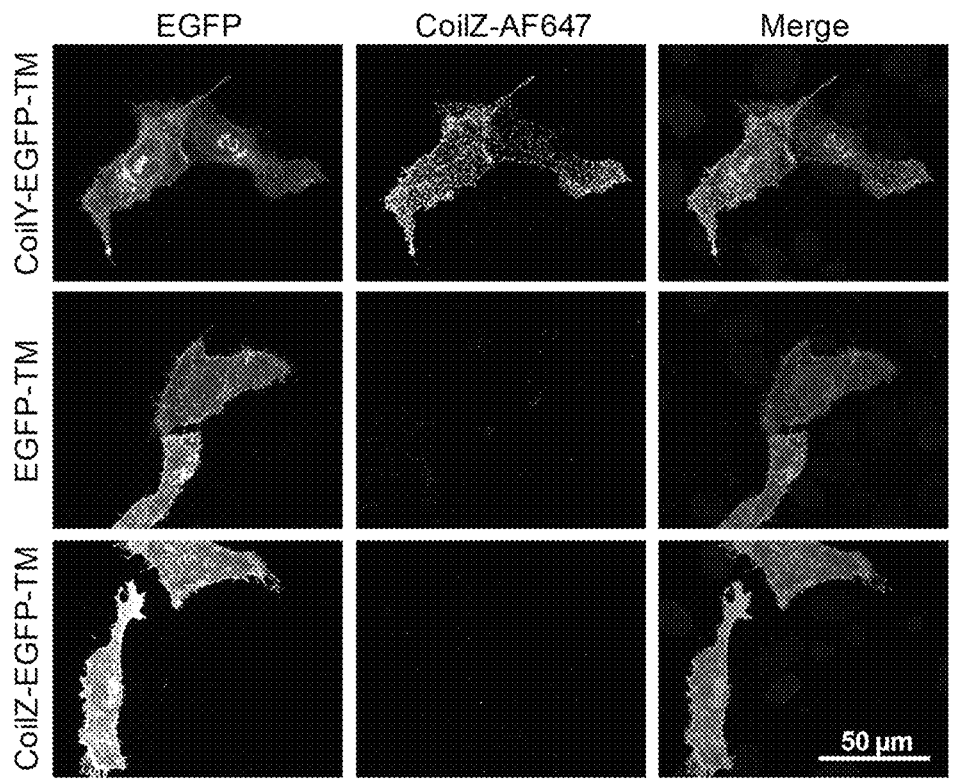
FIG. 3B is a set of images showing CoilY-GFP binding to CoilZ-AF647. CoilZ is also referred to herein as Coil6 and CoilY is also referred to herein as Coil5.

Fluorescence microscopy was used to confirm that the VIP Y/Z tag set enabled selective fluorescent labeling of proteins (FIGS. 3A and 3B). CoilZ was expressed by fusion to a cell-surface localized variant of GFP (CoilZ-GFP; pDisplay vector). Cell-surface displayed CoilZ-GFP was visualized with a CoilY-AlexaFluor 647 (CoilY-AF647) probe peptide (FIG. 3A). Labeling was rapid (<30 min), target-specific, and live-cell compatible. Homodimerization between a CoilZ probe peptide and CoilZ-GFP was not observed. Cells expressing untagged GFP were not labeled with the CoilY probe peptide. CoilY was also expressed fused to the cell surface localized GFP and visualized using a CoilZ-AF647 probe peptide (FIG. 3B). No homodimerization of CoilY was observed, and the labeling was specific.

Figure 4:
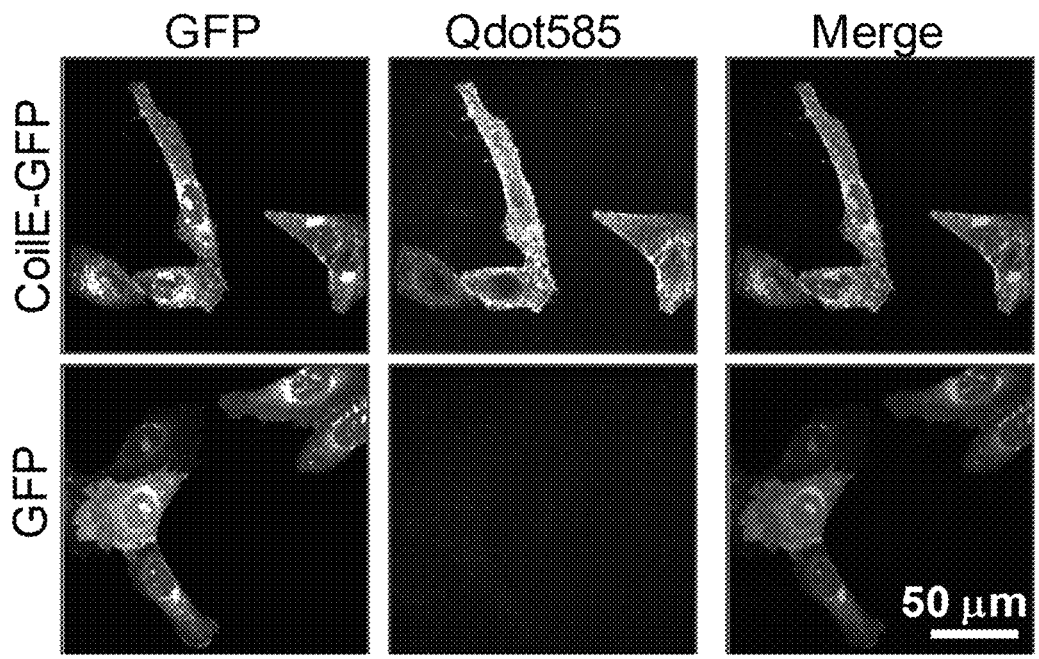
FIG. 4 is a set of images showing CoilE-GFP binding to CoilR-biotin as detected by subsequent binding to streptavidin Qdot585.
Figure 14:
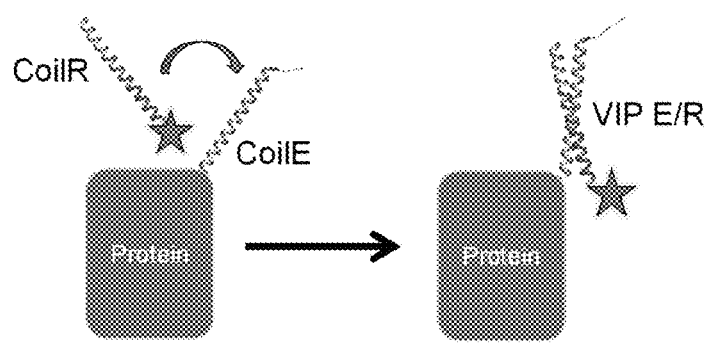
FIG. 14 is a schematic showing the principle of VIP E/R tagging. CoilE is genetically encoded into the protein of interest to act as a fusion tag. CoilR is purified and conjugated to a reporter molecule and acts as the probe. Incubation of CoilE-tagged protein with CoilR leads to the formation of the VIPE/R heterodimer, thus labeling the protein with a detectable reporter.

CoilE and CoilR form a coiled-coil heterodimer, called VIP E/R, as shown in FIG. 14. The VIP E/R tag set was similarly validated. CoilE was expressed as fused to the cell surface localized variant of GFP (CoilE-GFP; FIG. 4) and visualized using CoilR-biotin (prior to fixation) followed by streptavidin-Qdot585.

Figure 5A:
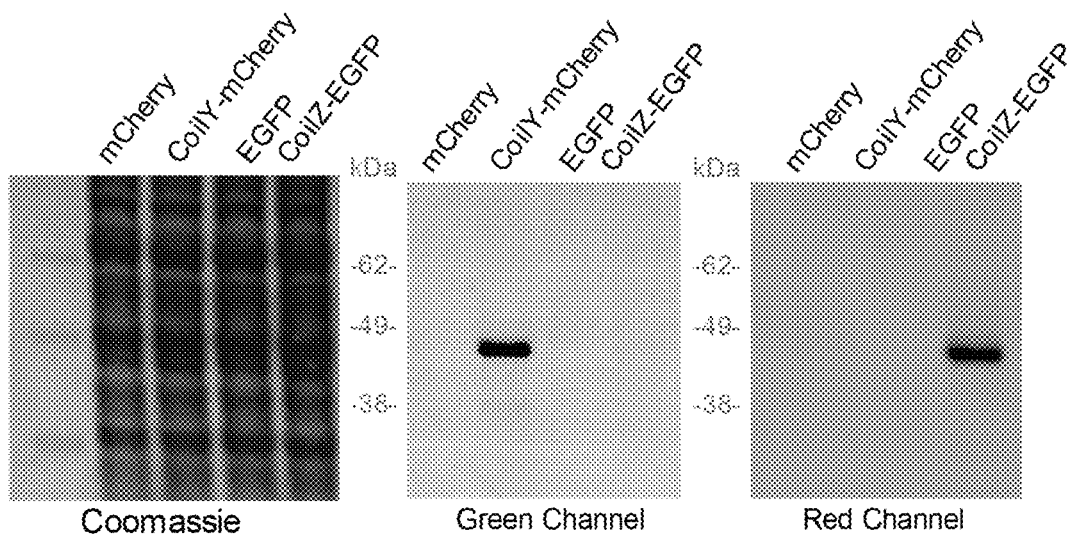
FIG. 5A left panel is an image of a Coomassie stained gel of HEK293 lysates expressing the constructs indicated at the top of the gel. The middle panel shows binding of CoilZ-fluorescein to CoilY-mCherry. The right panel shows CoilY-rhodamine labeling CoilZ-EGFP.
Figure 23:
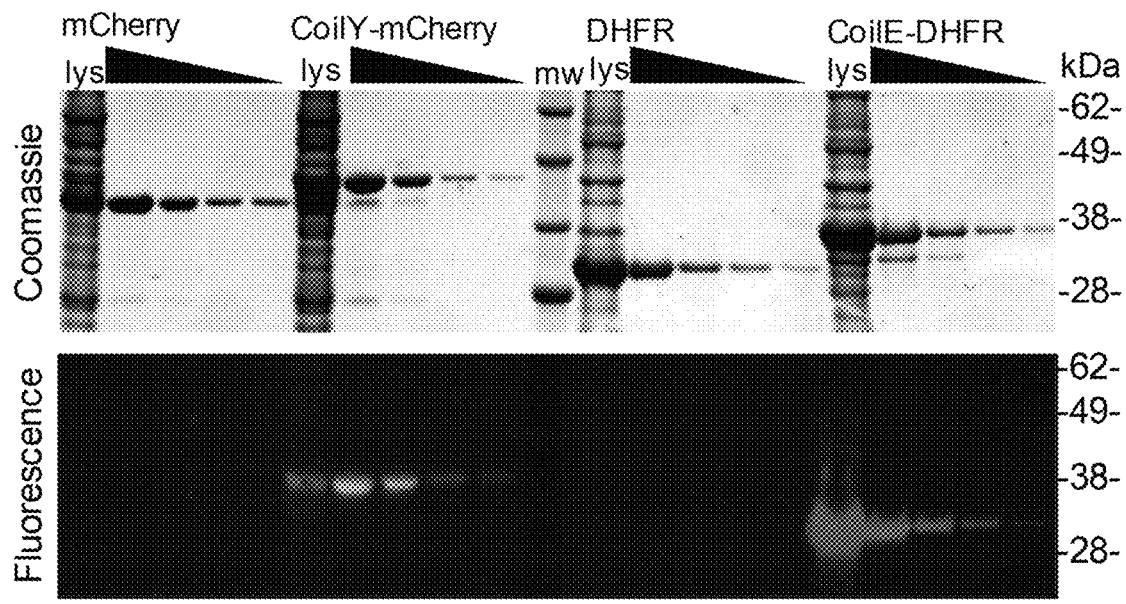
FIG. 23 provides data indicating that VIP Y/Z and VIP E/R can be used together to label two distinct protein targets (CoilY-mCherry and CoilE-DHFR) specifically. Crude lysates (lys.) and purified proteins (serial dilutions) were resolved by SDS-PAGE. Lysates were prepared from HERK 293FT cells transfected with mCherry, CoilY-mCherry, DHFR, and CoilE-DHFR. The protein gel was transferred to a PVDF membrane and then incubated with CoilZ-Fluorescein and CoilR-rhodamine. After washing, the membrane was imaged to detect VIPER labeling of DHFR (red) and VIP Y/Z labeling of mCherry (green). Untagged proteins were not labeled by either CoilR-rhodamine or CoilZ-fluorescein.

It was next confirmed that the VIP Y/Ztag set could be used to specifically label two model proteins simultaneously (FIG. 5A). A protein gel-based assay was optimized for analyzing VIP tags in vitro. Cell lysates were made from cells transfected with mCherry, CoilY-mCherry, GFP, or CoilZ-GFP, resolved by SDS-PAGE, and transferred to a membrane. GFP and mCherry fluorescence were not preserved in this experiment. The membrane was then contacted with CoilZ-fluorescein and CoilY-rhodamine before imaging. Probe peptide binding was detected for both CoilY-mCherry (with CoilZ-fluorescein) and CoilZ-GFP (with CoilY-rhodamine). The probe peptides were specific for each tagged protein, and this single pair enabled specific and selective protein tagging of two distinct targets. In addition both the VIP E/R and VIP Y/Z tag sets could be used concurrently to label two recombinant proteins (DHFR and mCherry) without crosstalk (FIG. 23).

Figure 5B:
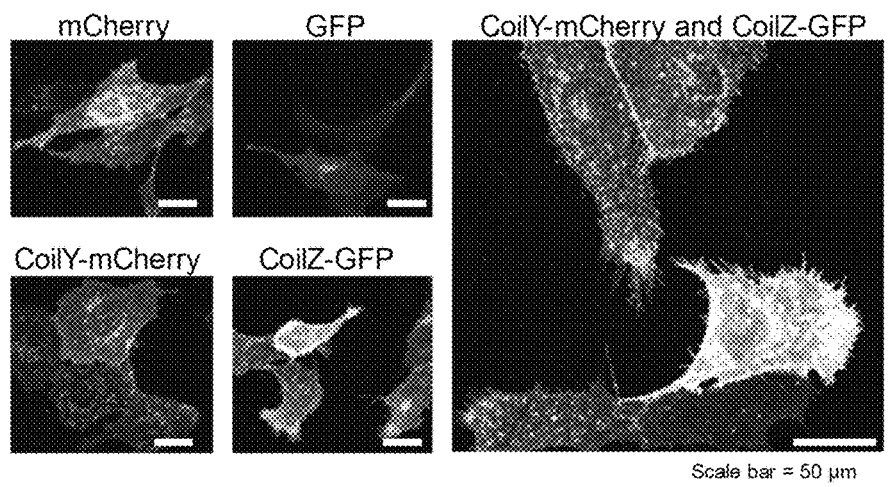
FIG. 5B is a set of fluorescent micrographs of U-2 OS cells transfected with EGFP, mCherry, CoilY-mCherry, or CoilZ-EGFP, with the largest micrograph showing a mixture of singly-transfected CoilY-mCherry and CoilZ-EGFP cells.
Figure 9:
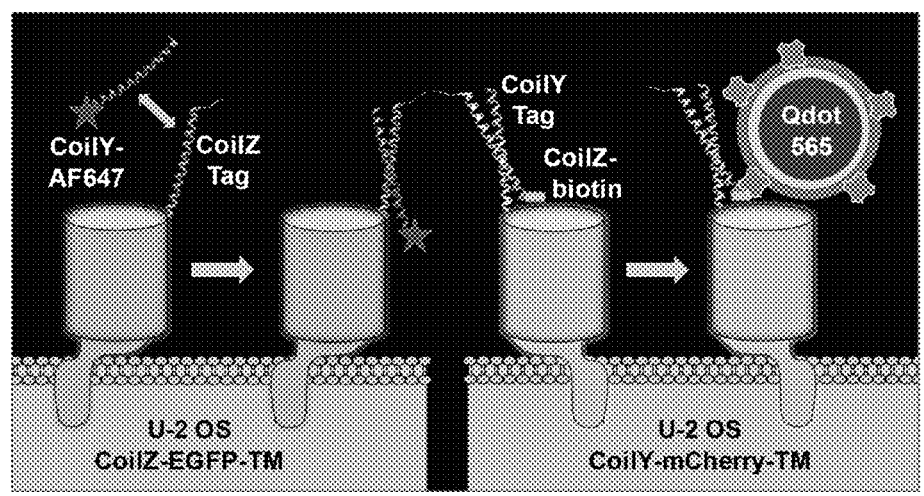
FIG. 9 is a schematic showing an example of a heterodimerization reaction using the provided compounds to label two distinct targets (CoilY-mCherry-TM and CoilZ-EGFP-TM; TM refers to a transmembrane domain).
Figure 13:
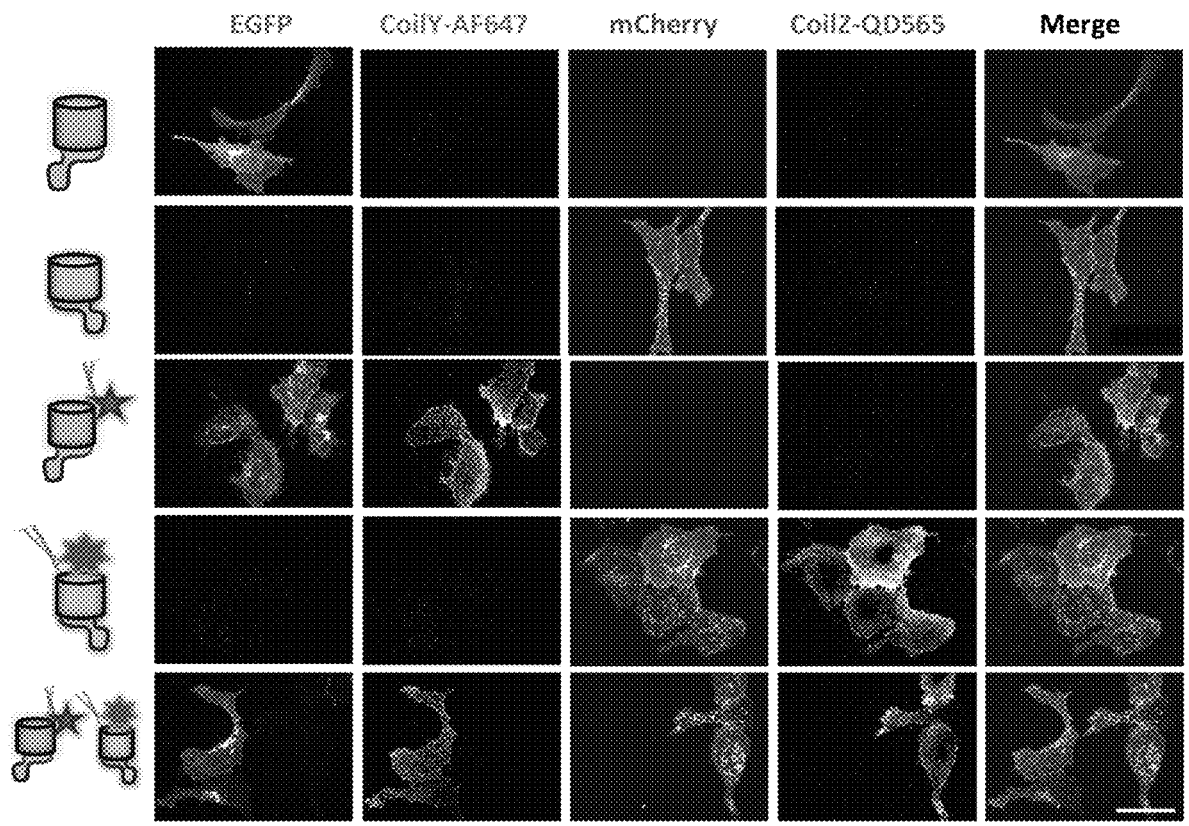
FIG. 13 is a set of 25 images showing Zip6-EGFP binding to Zip5-Af647 and Zip6-mCherry binding to Zip6-biotin as visualized by streptavidin Qdot565. The first and second (from the top) rows (10 images) show that no probe peptide binding was observed when labeling untagged EGFP and mCherry. The third and fourth rows (from the top) show CoilZ-EGFP or CoilY-mCherry (single populations). The bottommost panel shows a mixture of CoilZ-EGFP and CoilY-mCherry expressing cells labeled specifically by their respective probe peptides when treated by both. The scale bar is 50 µm.

It was next confirmed that the VIP Y/Z tag set could be used in two-target imaging in fixed cells (FIGS. 5B and 13). A combination of cell lines singly-transfected with mCherry, GFP, CoilY-mCherry, or CoilZ-GFP was used, as illustrated in FIG. 9. The untagged FPs (mCherry and GFP) did not interact with either CoilZ-biotin or CoilY-AF647. As expected, we found that CoilZ-biotin specifically labeled CoilY-mCherry, and homodimerization with CoilY-AF647 was not observed. Similarly, CoilZ-GFP was labeled by CoilY-AF647 and not by CoilZ-biotin. Then we labeled two tagged FPs in one sample using a mixed population of cells expressing either CoilY-mCherry or CoilZ-GFP. As demonstrated in FIG. 5B, CoilY and CoilZ self-sort into specific heterodimers, thus enabling use of these peptides together to label two discrete targets.

Using VIP Y/Z, we labeled proteins with organic fluorophores (fluorescein, rhodamine, and AF647) and Qdots (Qdot565). The reporter chemistry can be selected and optimized for different applications (see FIG. 1), which makes this technology versatile.

Example 3—VIP 1/2 and VIP 3/4 Tag Sets

Optimization of the VIP 1/2 (including Coil1 and Coil2) and VIP 3/4 (including Coil3 and Coil4) will be performed as described in Example 1 above. Additional VIP tag sets can be assessed in transfected cell lines by flow cytometry and confocal fluorescence microscopy. For fluorescent detection, probe peptides can be conjugated to organic fluorophores or Qdots using standard bioconjugation reactions. Live-cell imaging can be used to confirm that the protein tags do not alter normal protein localization, trafficking, or function. A variety of different proteins of interest can be used in validation, including GFP, TfR1, a receptor tyrosine kinase, such as EGFR, as well as other proteins.

The disclosed tag sets preferentially label cell surfaces and are membrane impermeant in living cells, which is of particular use in labeling cell-surface receptors (i.e., TfR1 and EGFR) and more particularly of use in monitoring trafficking and endocytosis.

Example 4—Use of the Disclosed Compositions and Methods to Label Components Involved in Iron Uptake within a Cell Iron is required for cell survival, but an excess is toxic and causes life-threatening human diseases. Therefore, cells have fine-tuned control mechanisms for regulating iron that rely on nano-assemblies of proteins. Iron uptake starts on the cell surface upon docking of iron-bound transferrin (Tf) to the transmembrane receptors transferrin receptor 1 (TfR1) and TfR2. The labeling technology will be validated by first imaging components of the TfR1 pathway, which are well-characterized. Oxidized iron (Fe') is bound by Tf (FIG. 2, component 1), the major iron transport protein in blood. In the absence of Tf, TfR1 (component 2) forms a complex with the protein HFE (component 3). Tf competes for binding of HFE to TfR1. The Tf/TfR1 complex internalizes through clathrin-coated vesicles. These endosomes acidify, which potentiates the release of $Fe^{3+}$ from the Tf/TfR1 complex. $Fe^{3+}$ is reduced by STEAP3 (component 4) and transported into the cytoplasm by ZIP14 (component 5) or DMT1 (component 6). In the cytoplasm $Fe^{2+}$ is delivered to either iron-requiring proteins or stored within ferritin. Then the apo-Tf/TfR1 complex recycles to the cell surface. The neutral pH of the extracellular environment facilitates release of apo-Tf from TfR1, enabling the process to start again.

The sequence of the ectodomain of TfR2 (component 7 in FIG. 2) is over 60% homologous to TfR1. TfR2 also binds to transferrin, but with lower affinity. TfR2 can also be imaged using the VIP tags. TfR2 is thought to be functionally distinct from TfR1, and VIP tags can be used to simultaneously image these receptors in cells to define differences in localization or trafficking.

Example 5—Use of the Disclosed Compositions with TfR1

Figure 2:
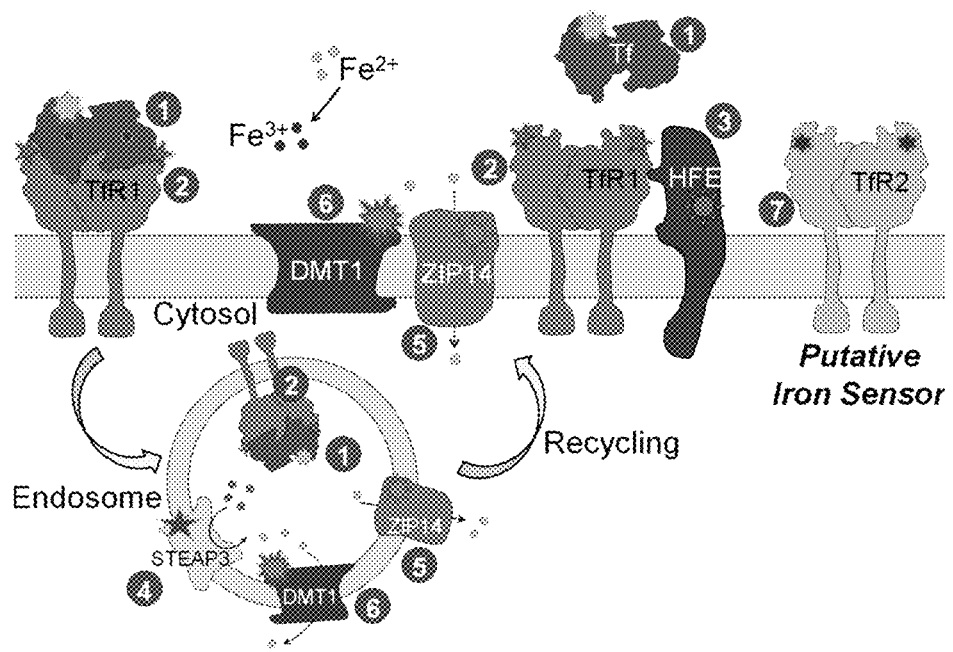
FIG. 2 is a schematic showing an iron uptake pathway. Numbers highlight proteins that might be labeled using distinct, orthogonal versatile interacting peptide (VIP) tags.

Proteins involved in iron homeostasis that have known localization and dynamics can be imaged according to the disclosed methods. Such proteins include those of the TfR1 iron uptake pathway (FIG. 2). TfR1 was selected as the first transmembrane receptor to be imaged because it is a well-studied receptor with defined localization and trafficking behaviors. TfR1 can be tagged with VIP E/R pair, a tag set described herein and in Example 1 above.

Iron uptake can be induced in stably transfected cell lines by the addition of purified Tf. Tf is commercially available conjugated to a variety of chemical reporters (e.g., Tf-AF488 or Tf-AF647). Tf can be conjugated to a pH-activated probe, such as pH, Rodo® Red or a BODIPY that remains non-fluorescent above pH 6.0. Use of pH-sensitive probes can be used to monitor internalization and acidification of endosomes in real-time.

Interactions between Tf and tagged TfR1 (i.e., TfR1-CoilE labeled by CoilR-AF488) can be visualized to confirm that the tagged receptor retains normal localization and function. Upon docking, co-localization of fluorescence and receptor internalization should be observable. Compartmental markers (e.g., Rab5 for early endosomes) can be used to follow this process by live-cell imaging. In subsequent studies, TfR1 can be imaged with other targets in the TfR1 pathway.

Example 6—Comparing the Sub-Cellular Localization of TfR2 to that of TfR1

Figure 6:
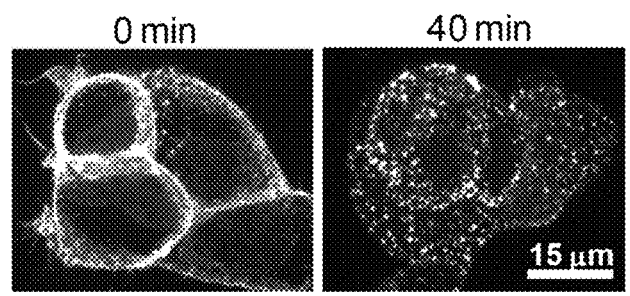
FIG. 6 is a set of two fluorescent micrographs of a TfR2-CoilZ, a transmembrane receptor, labeled with CoilY-(AlexaFluor647) before (left, 0 min) and after (right, 40 min) internalization. Nuclei were stained with Hoechst.

The disclosed methods can be used to define how Tf-binding influences the localization of TfR1 or TfR2. TfR2 localization was visualized using the VIP Y/Z tag set (FIG. 6). TfR2 was tagged with CoilZ at the C-terminus (TfR2-CoilZ). The C-terminus of TfR2 is extracellular. The construct was stably-transfected into HEK293 cells. Transfected cells were cooled to 4° C. to halt endocytosis and then TfR2 was contacted with CoilY-AF647. Fluorescent images were obtained and showed cell-surface expression of fluorescent TfR2 (white) both immediately following labeling (FIG. 6, left) and in endocytic vesicles after 40 min at 37° C. (FIG. 6 right).

The sub-cellular localization of TfR2 compared to TfR1 can then be determined. TfR2 (#7) and TfR1 (#2) can be imaged in the presence and absence of Tf (#1) (FIG. 2). Three-color imaging could be informative on the movement of receptors after Tf binding. Initially, three targets can be imaged by confocal fluorescence microscopy and by super-resolution microscopy (SRM). SRM is a set of imaging methods (e.g., PALM or STORM) that enable nanometer (~30 nm) resolution by sequential imaging and localization of single fluorophores followed by image reconstruction. Multi-color SRM typically uses organic fluorophores, and VIP tags can be used with a variety of SRM-compatible fluorophores. TfR1-CoilE can be contacted with (for example) AF647, Tf with Atto488 (e.g., Tf-Atto488), and TfR2-CoilZ with DyLight750.

Example 7—Using the Disclosed Compositions and Methods to Track Protein Location by EM and CLEM Fluorescence microscopy enables researchers to observe specific proteins, but without an ultrastructural context. Fluorescent micrographs reveal only a few features at a time while the rest of the cell remains invisible. In contrast, EM illuminates sub-cellular structures, including organelles, membranes, and macromolecules. Correlative fluorescence and EM (i.e., CLEM) combines the best features of both fluorescence microscopy and EM.

A central limitation in EM and CLEM is the lack of genetically-encoded tags that can be used to identify specific proteins in gray-scale EM micrographs. Creating target-specific contrast for EM requires a new technology for delivering electron-dense stains to cellular proteins. There are very few genetically-encoded protein tags for EM and proteins are typically identified by immunolabeling—but immunolabeling has many drawbacks (specificity, artifacts, etc.). One of the challenges of using immunomarkers is the large size of IgG, which is 14 nm long and 155 kDa, which diminishes the precision of EM. Secondary detection is a standard technique used to amplify signal and conserve primary antibodies, however this technique can offset the reporter particle 15-50 nm away from the target. There have been attempts to develop metal-chelating protein tags using ferritin or metallothionein fusions, but these tags have not been widely adopted due to multimerization, size, metal toxicity, and poor signal-to-noise.

More recent EM tags use oxidation of DAB to form an insoluble polymer, which can be stained subsequently with osmium tetroxide to generate contrast. DAB precipitation is difficult to control, which can limit the ability to precisely determine location of a structure within a cell. However, a limited set of genetically-encoded tags have successfully used DAB oxidation for protein-specific staining (e.g., APEX, miniSOG, FLIPPER, and the tetracysteine tag). The APEX tag (28 kDa) uses peroxidase activity (instead of light) to polymerize DAB for EM. MiniSOG is a 15 kDa tag with dim fluorescence for CLEM imaging. The tetracysteine tag is small, but has poor specificity. FLIPPER combines an FP with a peroxidase for DAB precipitation. This CLEM tag is over 70 kDa and can only be used to tag secreted proteins. The biggest drawback to all of these EM tags is that they use the same reporter chemistry, which makes them one-color.

The disclosed compounds and methods offer an improvement over the above methodologies because they provide multi-color EM and CLEM. Target proteins will be labeled with EM-visible reporters such as gold particles (EM), Qdots (CLEM), or fluoronanogold (CLEM). This compatibility with numerous reporters makes the technology versatile and allows end-users to select reporters for distinct applications.

Figure 7A:
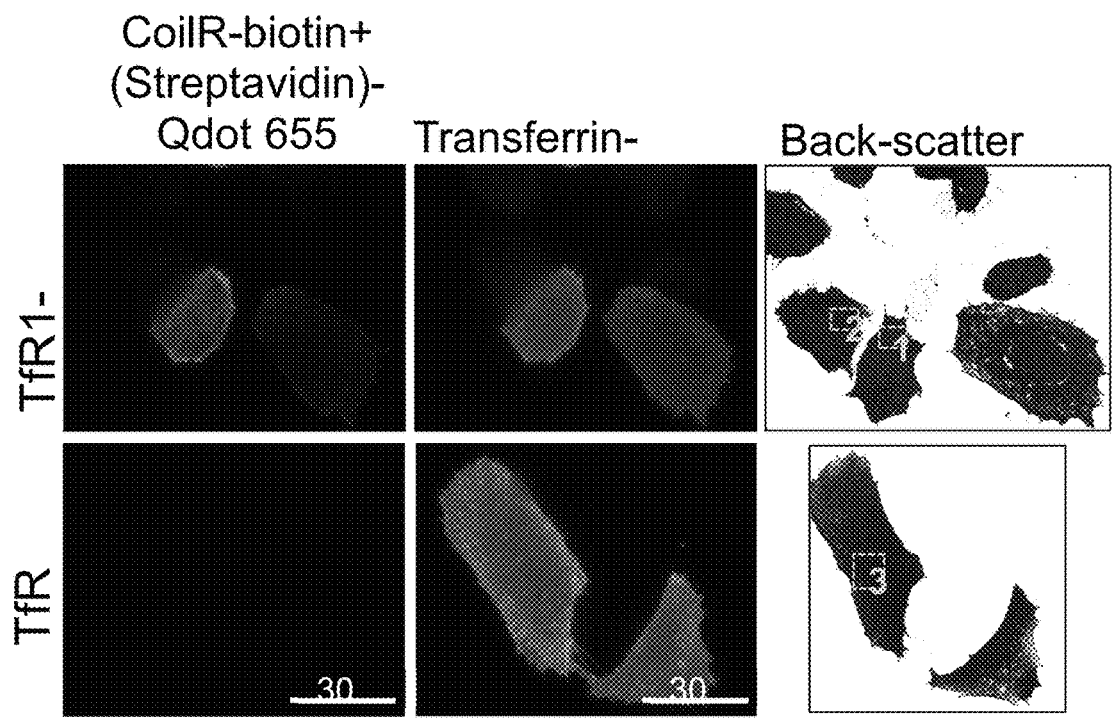
FIG. 7A are images showing CHO TRVb cells expressing Transferrin Receptor 1 (TfR1)-CoilE. VIP-tagged TfR1 bound Tf-AF488 and CoilR-biotin, which was visualized by streptavidin-conjugated Qdot655. TfR1 labeling, mediated by VIPER, is shown in the left column while fluorescent transferrin (Tf-488) is in the middle column. The right column shows the cells imaged by back-scatter detection using an electron microscope. Cells expressing untagged TfR1 (bottom row) were not labeled by Qdot655.
Figure 7B:
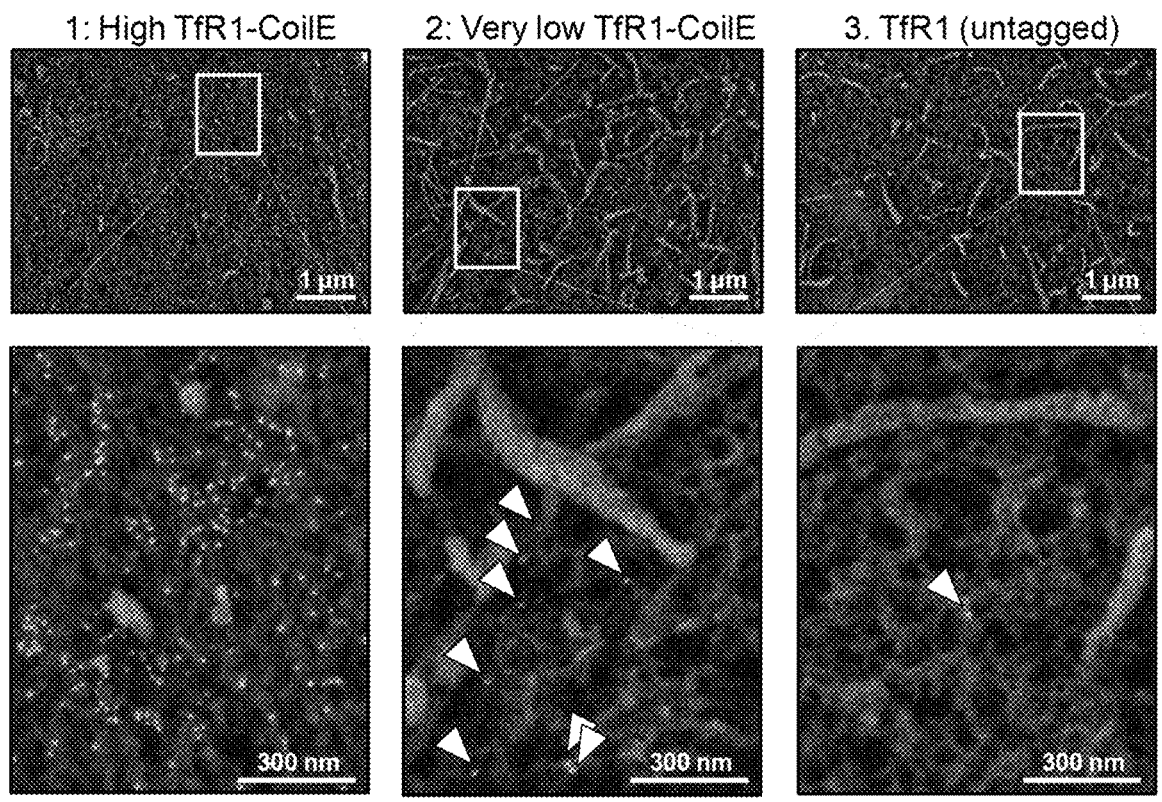
FIG. 7B shows a scanning electron micrograph of cells indicated in FIG. 7A. Bottom panels are magnified views of the areas shown in the top images. Cells expressing high levels of TfR1-CoilE [1; left column] had very dense Qdot-labeling (white dots), while cells with little TfR1-CoilE expression [2; middle column] showed only a few Qdots (highlighted with arrowheads in the enlarged inset). The SEM micrograph of TfR1 (untagged) [3; right column] shows that untagged receptor was not labeled by streptavidin-Qdot655. A single Qdot was observed by SEM, as indicated by the arrowhead in the lower, rightmost panel.

Quantum dots were used to demonstrate that VIP E/R can be used for both CLEM and EM (FIGS. 7A and 7B). CHO TRVb cells expressing Transferrin Receptor 1 (TfR1)-CoilE. VIP-tagged TfR1 were treated with Tf-AF488 and CoilR-biotin, which was visualized by streptavidin-conjugated Qdot655. TfR1 labeling, mediated by VIPER, is shown in the left column while fluorescent transferrin (Tf-488) is in the middle column. The right column shows the cells imaged by back-scatter detection using an electron microscope. Cells expressing untagged TfR1 (bottom row) were not labeled by Qdot655.

Cells expressing high levels of TfR1-CoilE (FIG. 7B: 1; left column) had very dense Qdot-labeling (white dots), while cells with little TfR1-CoilE expression (FIG. 7B: 2; middle column) showed only a few Qdots (highlighted with arrowheads in the enlarged inset). The SEM micrograph of TfR1 (untagged) (FIG. 7B: 3; right column) shows that untagged receptor was not labeled by streptavidin-Qdot655. A single Qdot was observed by SEM, as indicated by the arrowhead in the lower, rightmost panel.

Figure 8:
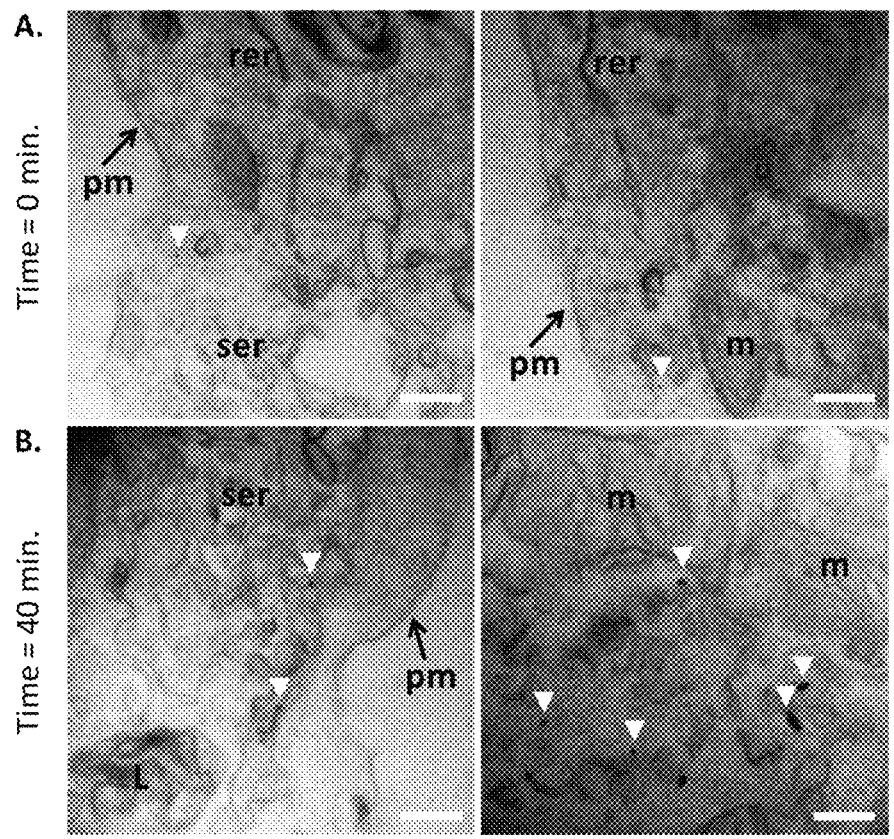
FIGS. 8A and 8B are TEM images of TfR2-CoilZ labeled with CoilY-biotin and streptavidin-gold (10 nm). Cells were labeled at 4° C. to prevent endocytosis during labeling. Cells were fixed immediately after TfR2 imaging (FIG. 8A) or after 40 minutes at 37° C.

VIP Y/Z can be used to monitor receptor trafficking and localization by transmission electron microscopy (TEM) (FIG. 8). For this study, TfR2-CoilZ-expressing HEK 293 was used. Live cells were cooled to 4° C. to halt endocytosis and then TfR2-CoilZ was selectively gold-labeled by incubation with CoilY-biotin and streptavidin-gold. Following fixation, cells were processed into Epon resin and 90 nm ultrathin sections were imaged using an FEI Tecnai. Cells that were fixed immediately after labeling had gold-labeling within 100 nm of the plasma membrane, consistent with minimal internalization of TfR2. A second set of cells was warmed to 37° C. to promote TfR2 uptake. After 40 minutes, cells were fixed and gold-labeled TfR2 was found in two clusters: one within 100 nm of the plasma membrane and another further within cells (FIG. 8).

Example 8—Using the Disclosed Compositions and Methods to Determine the Mechanism of Endocytosis of a Transmembrane Receptor The disclosed compositions and methods can be used in imaging Tf/TfR1 localization on the cell surface, in early endosomes, and in recycling endosomes. TfR1 is thought to undergo clathrin-dependent endocytosis and the disclosed compositions and methods can be used to observe TfR1 in clathrin-coated pits. TfR1-CoilE labeled can be labeled with CoilR-[10 nm Gold] or CoilR-biotin for subsequent detection with a streptavidin conjugated label such as a gold or quantum dot label). Samples can be processed to retain cellular ultrastructure so that structures (e.g., clathrin-coated pits and endocytic vesicles) are preserved for EM staining.

The trafficking and degradation of other transmembrane receptors occurs in response to ligand binding. Often, when a receptor is being studied there is a controversy on whether receptor endocytosis is clathrin- or caveolin-dependent.

High-resolution EM imaging of such a transmembrane receptor can be used to describe how itis internalized in the presence or absence of ligand. TfR1 can be imaged in combination with Tf, and the other transmembrane receptor using, for example, TfR2-CoilZ, TfR1-CoilE, and Tf covalently attached to an EM reporter. A cell line that stably expresses both receptors at endogenous levels can be generated. CLEM images can be obtained using Qdots (i.e., Qdot525, Qdot565, and Qdot655), which can be distinguished based on fluorescence emission, size, and shape.

The same cell line can also be imaged by high-resolution transmission EM (TEM). TEM images can in turn allow imaging within cells to identify sub-cellular compartments (e.g., early and late endosomes) involved in iron homeostasis or other receptor-mediated processes. Against the TEM images, TfR1, transmembrane receptor, and Tf can be identified using distinctly-sized gold particles (e.g., 5 nm, 10 nm, and 20 nm). Alternatively, they can be imaged by CLEM using a "fluoronanogold" approach that involves a fluorescent reporter peptide conjugated to gold.

Example 9—Multi-Color EM and Correlative Light and EM (CLEM)

The disclosed compositions and methods can be used in labeling five or more targets in a single image. For example, components of the iron uptake pathway can be imaged using one or more of the disclosed tag sets (VIP E/R, VIP Y/Z, VIP 1/2, and/or VIP 3/4) alone or in combination with another labeling method. In some examples, proteins of interest conjugated to one or more of the disclosed polypeptides can be expressed in a single cell line.

Alternatively, two of the VIP tag sets can be used: for example, TfR1 can be labeled with CoilE and TfR2 with CoilZ. Other targets, particularly cell surface targets, can be detected by immunolabeling. Such cell surface targets in the TfR1 and TfR2 pathway can include clathrin, HFE, or other target proteins. Lastly, other proteins of interest such as Tf, a soluble ligand, can be directly conjugated to an EM reporter. Intracellular targets can be imaged using permeabilized cells or with a probe peptide that includes an intracellular peptide targeting sequence.

Protocols used to retain fluorescence while highlighting ultrastructure for EM are known in the art, particularly for use with CLEM. Larger probes such as fluorescent proteins or a 50 nm Qdot can change trafficking behavior if used as a label in live cells. If such altered trafficking of a protein of interest is observed, then a smaller label such as a nanogold particle, can be used.

Example 10—Versatile Interacting Peptide Tag Sets for Use in Fluorescent Microscopy The disclosed methods were tested in transfected human osteosarcoma cells (U-2 OS). A pDisplay vector was used to target CoilZ-EGFP and untagged EGFP to the cell surface. This construct includes a C-terminal fusion to the transmembrane domain of the platelet derived growth factor receptor. As expected, both CoilZ-EGFP and untagged EGFP localized to the cell surface, and green fluorescence was observed within 24 h of transfection. Then the cells were blocked with 6% BSA and 10% FBS for 30 minutes at 37° C. and then contacted with an AF647-conjugated CoilY probe (CoilY-AF647), 30 min at 4° C. Cells were fixed before imaging by confocal fluorescence microscopy. The probe peptides are membrane impermeant; only cell-surface EGFP was accessible to CoilY-AF647 for labeling. Colocalization of green fluorescent CoilZ-EGFP with CoilY-AF647 was observed. No CoilY-AF647 labeling was detected for untagged EGFP (FIG. 3A).

The CoilY/CoilZ tag set is bidirectional—either CoilZ or CoilY can serve as the probe peptide. CoilY-EGFP was expressed on the surface of U2OS cells and labeled with CoilZ-AF647. Protein labeling was rapid (<30 min) and specific; non-specific labeling of untagged EGFP was not observed. Homodimerization was not observed for either CoilZ-AF647 with CoilZ-EGFP or CoilY-AF647 with CoilY-EGFP (FIG. 3B).

Figure 12:
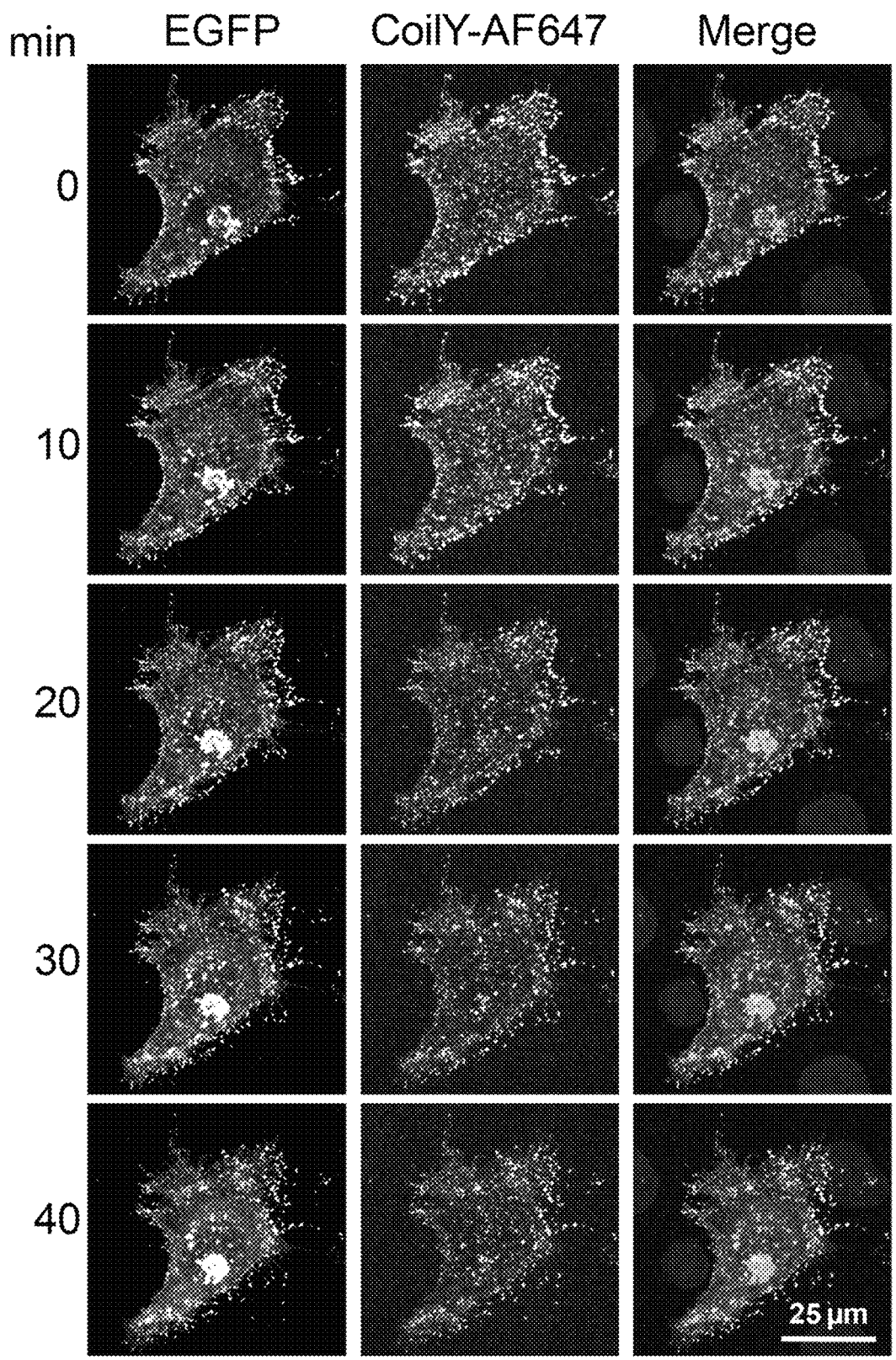
FIG. 12 is a set of 15 images showing time-lapse imaging (0 to 40 min) of CoilY/Z labeling in live cells. CoilZ-EGFP-TM was selectively labeled with 300 nM CoilY-AF647 and imaged every 10 min at room temperature. Overlay includes Hoechst (blue), EGFP (green), and AF647 (magenta). Scale bar represents 25 µm.
Figure 26:
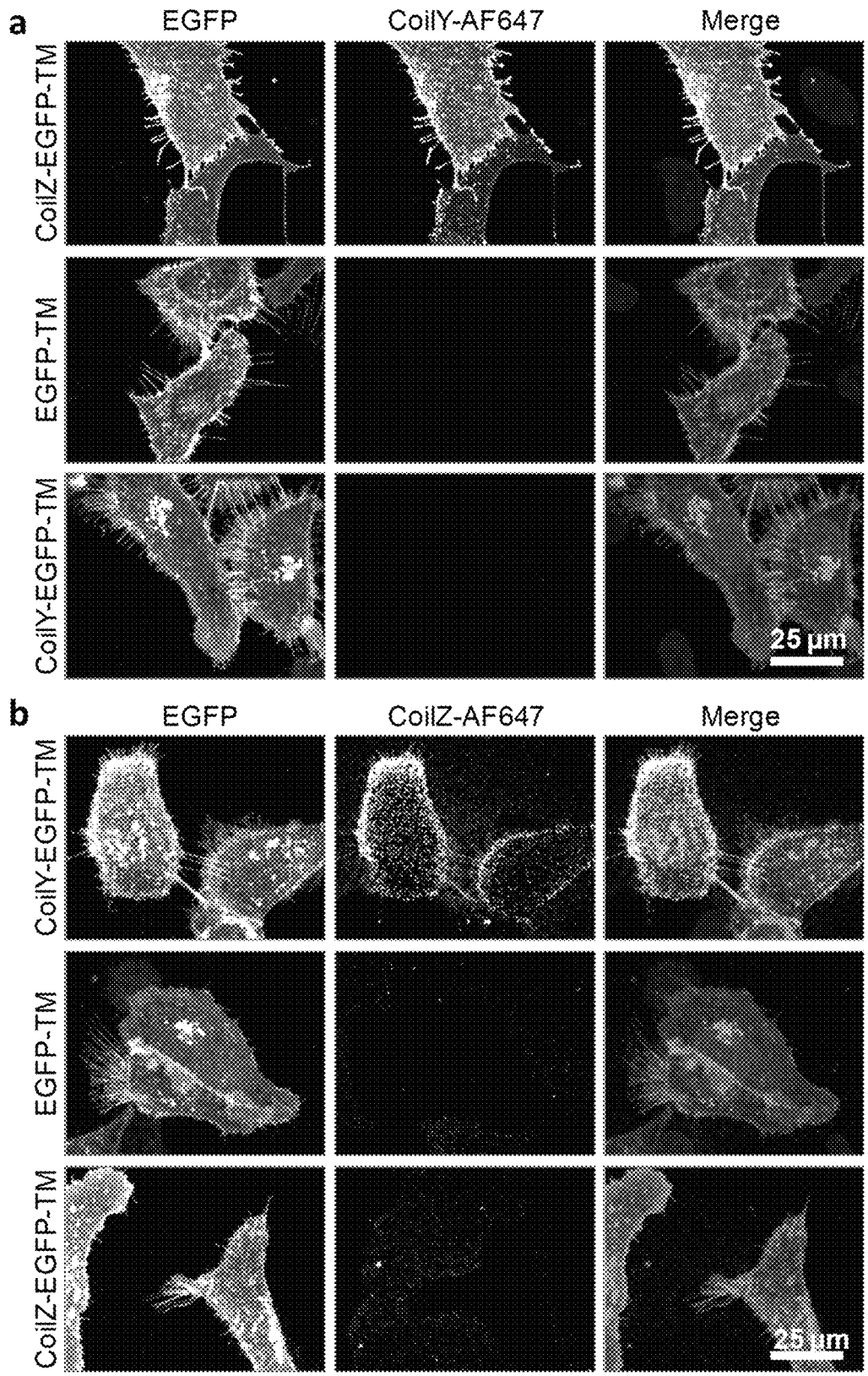
FIGS. 26A and 26B show the selective fluorescent labeling of cell-surface EGFP using CoilY and CoilZ.

The CoilY/CoilZ tag set is also compatible with live-cell imaging. CoilZ-EGFP was contacted with CoilY-AF647 in live U2OS cells. Imaging reveals rapid (<30 min), target-specific fluorescent labeling. Homodimerization was not observed for CoilY-EGFP incubated with CoilY-AF647. Non-specific labeling of untagged GFP was not observed (FIG. 26). Cells internalize labeled targets over time. CoilZ-GFP and CoilY-AF647 co-localization was observed on the surface and in endocytic vesicles due to rapid internalization, and AF647 signal accumulated inside cells during a 40 min. long incubation at room temperature (FIG. 12).

The VIPY/Z tag set can be used to label multiple protein targets simultaneously. Cells expressing CoilY-mCherry were combined with those expressing CoilZ-EGFP-pDisplay (FIG. 9). This mixed cell population, as well as unmixed CoilZ-GFP, CoilY-mCherry, and untagged controls, were plated for imaging. After blocking for 30 minutes at 37° C. with 6% BSA, 10% FBS, cells were treated at 4° C. with 500 nM CoilZ-biotin for 15 min and then 500 nM CoilY-AF647 for 15 min. The order of addition did not affect the labeling. Cells were then fixed, blocked for 1 hour with 6% BSA, 10% FBS and treated with Qdot565-conjugated streptavidin in order to label CoilZ-biotin. Fluorescence was detected by confocal fluorescence imaging. When faced with a mixture of CoilY and CoilZ tags, CoilY-AF647 and CoilZ-biotin can specifically label their respective targets, demonstrated by AF647/EGFP signal colocalization and Qdot565/mCherry colocalization (FIG. 13). There is no cross-reactivity between CoilZ-EGFP and CoilZ-biotin or CoilY-AF647 and CoilY-mCherry. No nonspecific labeling was observed in untagged GFP and mCherry. So the CoilY/Z tag set can be used to image up to four proteins at once.

Example 11. VIP Enables Multiple Targets to be Selectively Labeled in One Sample VIP Y/Z enables concurrent labeling of two targets, which is shown in FIG. 13 and FIG. 5A. Also, VIP Y/Z and VIPER can also be used for labeling two targets. The results are shown in FIG. 23. This feature is enabled because the peptide coils self-sort into specific heterodimeric pairs.

The peptides described in Table 1 are predicted to all self-sort into specific pairs. For example, VIP 1/2, VIP 3/4, and VIP Y/Z are predicted to form without the peptide coils cross-reacting, which will enable three (or more) distinct proteins targets to be labeled at once in a cell. For example, these tags might be used to image Tf (#1, direct labeled in vitro, such as Tf-AF488), TfR1 (#2), ZIP14 (#5), and TfR2 (#7) to study the iron uptake machinery (FIG. 2). A key feature is that the pairs only form specific heterodimers with each other, such as Coil1 dimerized with Coil2, Coil3 dimerized with Coil4, and CoilY dimerized with CoilZ.

Example 12. VIP Tags Enable an Alternative to Fluorescent Immunoblotting (e.g., Western Blotting)

Figure 10:
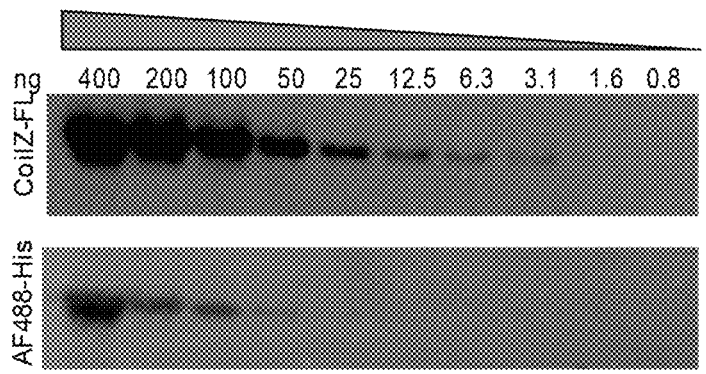
FIG. 10 is a detection limit comparison between peptide and immunolabeling. Serial dilutions of CoilY-mCherry (400 ng to 0.8 ng) were run on two identical SDS-PAGE gels before transfer to a PVDF membrane. The first membrane (top) was treated with CoilZ-fluorescein (CoilZ-FL) and imaged (ex 475/42 nm; em 537/35 nm). The second membrane (bottom) was labeled using an AF488-conjugated anti-His antibody "AF488-His" (QIAGEN, product number 35310) and imaged (475/42 nm excitation, 537/35 nm emission).

The disclosed method is a sensitive alternative to fluorescent immunoblotting. Purified $His_6$-CoilY-mCherry was generated and the sensitivity of detection of the $His_6$-CoilY-mCherry using our CoilZ-fluorescein was compared to that of an AF488-labeled anti-His antibody from Qiagen. CoilZ-fluorescein could detect as little as 3 ng of $His_6$-CoilY-mCherry, while the antibody required 8-fold more target protein (FIG. 10).

Specifically, purified His6-mCherry and His6-CoilY-mCherry were loaded on a 10% SDS-PAGE gel for separation. Electrophoresis occurred at 165 V for 1 h. The proteins were transferred from the gel onto a PVDF membrane (Immobilon-P, Millipore) at 80 V for 75 min. The membrane was blocked in 5% milk in TBST for 1 h. CoilZ-Fluorescein was diluted to 250 nM in 5% BSA in TBST and incubated with the membrane for 1 h. Fluorescent images were collected using FluorChem Q (blue channel: 475/42 nm excitation, 537/35 nm emission) imaging system after washing two times with TBST and twice with TBS.

Decreasing quantities of purified CoilY-mCherry (400 ng to 0.8 ng) were resolved by SDS-PAGE and transferred to a PVDF membrane. The membrane was blocked in 5% milk in TBST for 1 h. CoilY-mCherry was detected by blotting with anti-pentahistidine mouse antibody conjugated to AlexaFluor488 (1:5000, QIAGEN; product number 35310). Fluorescent images were collected using FluorChem Q (blue channel: 475/42 excitation, 537/35 emission) imaging system after washing twice with TBST and twice with TBS (FIG. 10).

Figure 20:
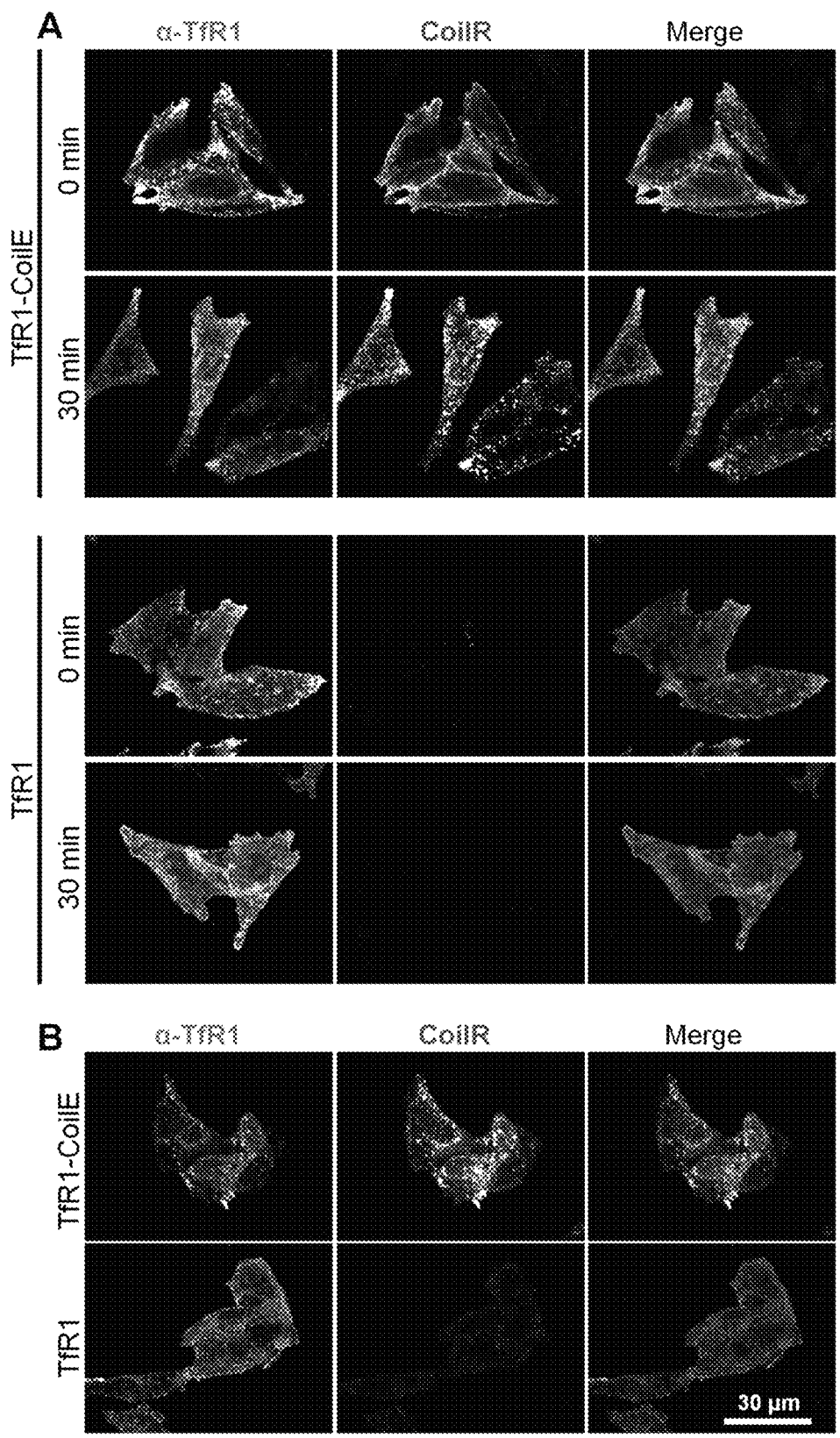
FIGS. 20A and 20B are images comparing immunolabeling to VIP E/R labeling in cells expressing TfR1 or TfR1-CoilE.
Figure 21:
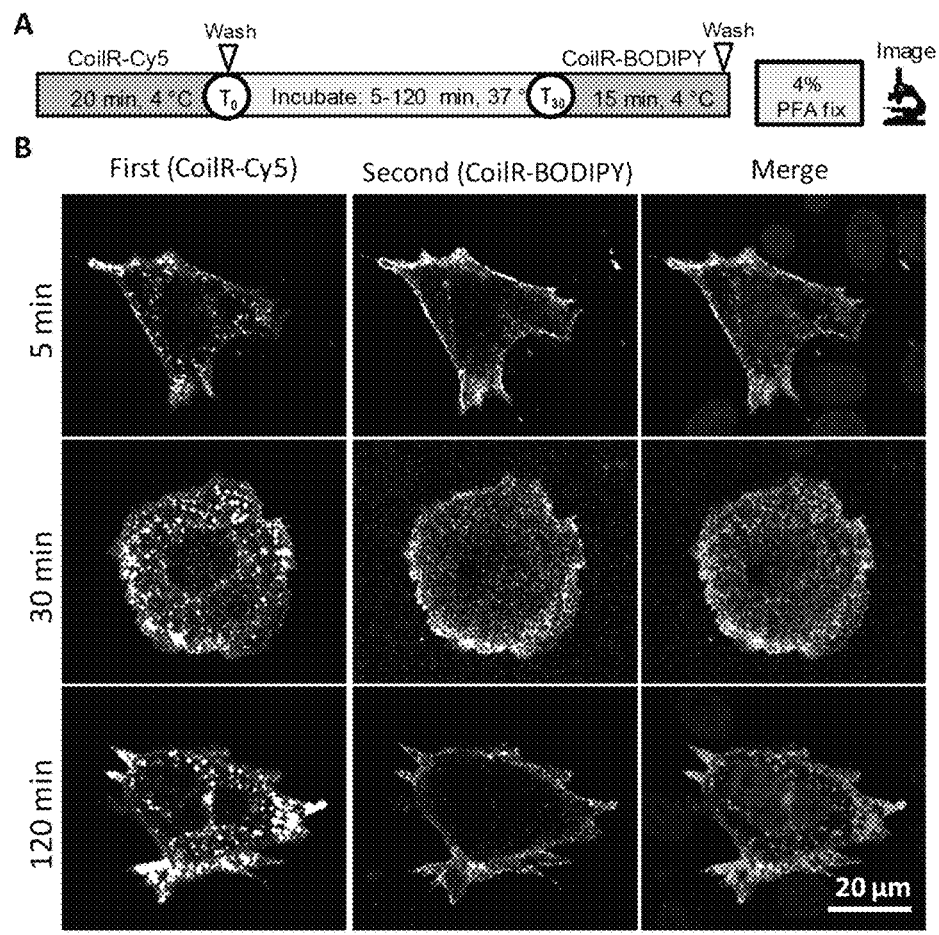
FIG. 21 are images showing VIP E/R can be used to image spatially- and temporally-distinct populations of TfR1. CHO TRVb expressing TfR1-CoilE were labeled with 500 nM CoilR-Cy5 for 20 minutes at 4° C. (first label). Cells were washed and returned to 37° C. incubation for 5, 30 and 120 minutes to enable the TfR1-CoilE receptor to resume movement (e.g., endocytosis). After incubation, cells were labeled with 500 nM CoilR-BODIPY (second label) at 4° C., washed, and fixed with paraformaldehyde. Fluorescence imaging shows that two distinct populations of receptors separated in time could be distinguished using a dual-color labeling approach. Cy5 was false-colored magenta and BODIPY was false-colored green, with overlapping signal indicated by white in the channel merge.
Figure 22:
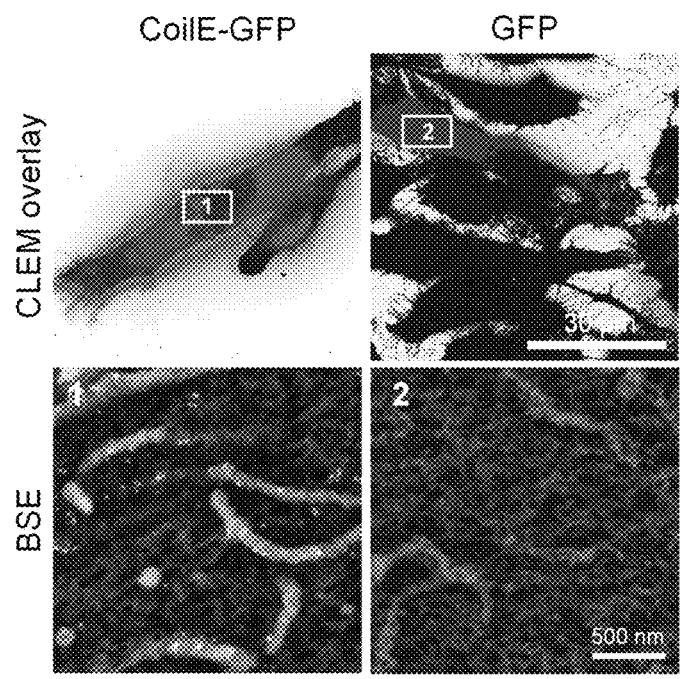
FIG. 22 are images showing CLEM imaging of cell-surface-displayed GFP with VIPE/R. U-2 OS cells expressing cell-surfaced displayed EGFP and CoilE-EGFP were treated with CoilR-biotin and Tf-AF488 at 4° C. before being fixed and labeled with streptavidin-QD655. Cells were imaged and mapped using a fluorescence microscope (FEI Corrsight) using MAPS software (FEI). Cells were then dehydrated and carbon-coated and imaged in a scanning electron microscope, where cells previously imaged by fluorescence were re-imaged with a backscattered electron detector (BSE). Fluorescence is overlayed over SEM (A), and the white inset shows area imaged at 65,000× (B). Quantum dots appear as small, bright white dots on cell surface. No QD655 could be detected on untagged EGFP.

Example 13. Versatile Interactive Peptide E/R (VIPER) Coiled-Coil Tag Facilities Labeling of Intracellular Proteins with Bright Chemical Reporters for Fluorescence Microscopy VIPER is a small, tight, coiled-coil tag. VIPER enabled fixed-cell intracellular labeling (FIG. 15), tracking membrane receptors in live cells (Figure FIG. 19, FIG. 20, FIG. 21), and enabled the first demonstration of a genetically-encoded, nanoparticle-based correlative light and electron microscopy (CLEM) tag (FIG. 22 and FIG. 7).

The utility of a new coiled-coil peptide tag system was established by generating fusions of CoilE to organelle-targeted fluorescent proteins and the iron transporter TfR1. The peptide tags are small (ca. 7 kDa), specific, and bind tightly with their complimentary binding partner. Efficient fluorescent tagging of CoilE with fluorophore-modified CoilR peptides was demonstrated in live and fixed cells.

Using VIPER, actin, histone, and mitochondrial targets were labeled in fixed, permeabilized cells (see FIG. 15) and transferrin receptor 1 (TfR1) was tracked through the endocytic pathway in live cells using fluorescence microscopy (FIG. 18-21). Using a biotinylated CoilR, cell-surface labeling of two targets, TfR1 and GFP, was demonstrated using streptavidin-conjugated Quantum dot, which allowed visualization of targets using CLEM (FIGS. 7 and 22). Towards the goal of developing versatile and robust protein labeling strategies, the use of an α-helical coiled-coil peptide pair (CoilY/CoilZ, i.e., CoilY/CoilZ) to fluorescently label cellular proteins was described herein.

Using one coil as the genetically-encoded tag and the other as the fluorescently-modified probe-peptide, it was demonstrated fluorescent labeling of proteins in cell lysates and on live cells. An additional pair, dubbed VIPER (CoilE/CoilR), has a reported binding affinity greater than that the CoilY/CoilZ pair. CoilE was designed from $EE_{12}RR_{345}L$ and CoilR was designed from $RR_{12}EE_{345}L_{12}$. CoilE and CoilR are small (5-8 kDa) and heterodimerize strongly, with a reported $K_D$ of $1.3 \times 10^{-11}$ M, suggesting that heterodimer formation is nearly irreversible. The interaction is illustrated in FIG. 14. Probe peptides were synthesized using overlap extension PCR and expressed recombinantly and purified from E. coli. Similar to CoilY/CoilZ, CoilR has short linker, a reactive cysteine handle for bioconjugation to reactive fluorophores, and a hexahistidine tag for affinity purification. Finally, a single cysteine was added that acts as a bioconjugation site, and thus can be attached to fluorophores or nanoparticles such as gold and Quantum Dots.

TABLE 2

Sequence and properties of heterodimerizing peptides.§

| Peptide | Sequence | MW (kDa) | pI |
|---|---|---|---|
| CoilE tag ($EE_{12}RR_{345}L$) | LEIEAAFLERENTALET RVAELRQRVQRLRNRVS QYRTRYGPL (SEQ ID NO: 2) | 5.20 | 10.6 |
| CoilR probe peptide | MGGSLEIRAAFLRQRNT ALRTEVAELEQEVQRLE NEVSQYETRYGPL*GGGA AALG*C*LAAAL*EHHHHHH (SEQ ID NO: 11) | 7.52 | 6.3 |
| Alternate CoilR probe peptide | MGGSLEIRAAFLRQRNT ALRTEVAELEQEVQRLE NEVSQYETRYGPL*GGGA AALG*K*LAAAL*EHHHHHH (SEQ ID NO: 12) | 7.52 | 6.27 |

§ Key: Peptide sequence, *linker sequence*, bioconjugationsite, Histag

TABLE 3

Sequence and properties of other heterodimerizing peptides.[§]

| Peptide | Sequence | MW (kDa) | pI |
|---|---|---|---|
| CoilY tag (SYNZIP-5) | NTVKELKNYIQELEERNA ELKNLKEHLKFAKAELEF ELAAHKFE (SEQ ID NO: 7) | 5.29 | 5.6 |
| CoilZ tag (SYNZIP-6) | QKVAQLKNRVAYKLKENA KLENIVARLENDNANLEK DIANLEKDIANLERDVAR (SEQ ID NO: 8) | 6.20 | 8.3 |
| CoilY probe peptide | MGSSNTVKELKNYIQELE ERNAELKNLKEHLKFAKA ELEFELAAHKFEGGGAAA CLGKLAAALEHHHHHH (SEQ ID NO: 13) | 7.83 | 6.4 |
| CoilZ probe peptide | MGSSQKVAQLKNRVAYKL KENAKLENIVARLENDNA NLEKDIANLEKDIANLER DVARGGGAAACLGKLAAA LEHHHHHH (SEQ ID NO: 14) | 8.74 | 8.0 |

[§] Key: Coil gene sequence, linker sequence, reactive cysteine, pET28b(+)-derived sequence, His$_6$ tag for purification.

Figure 15:
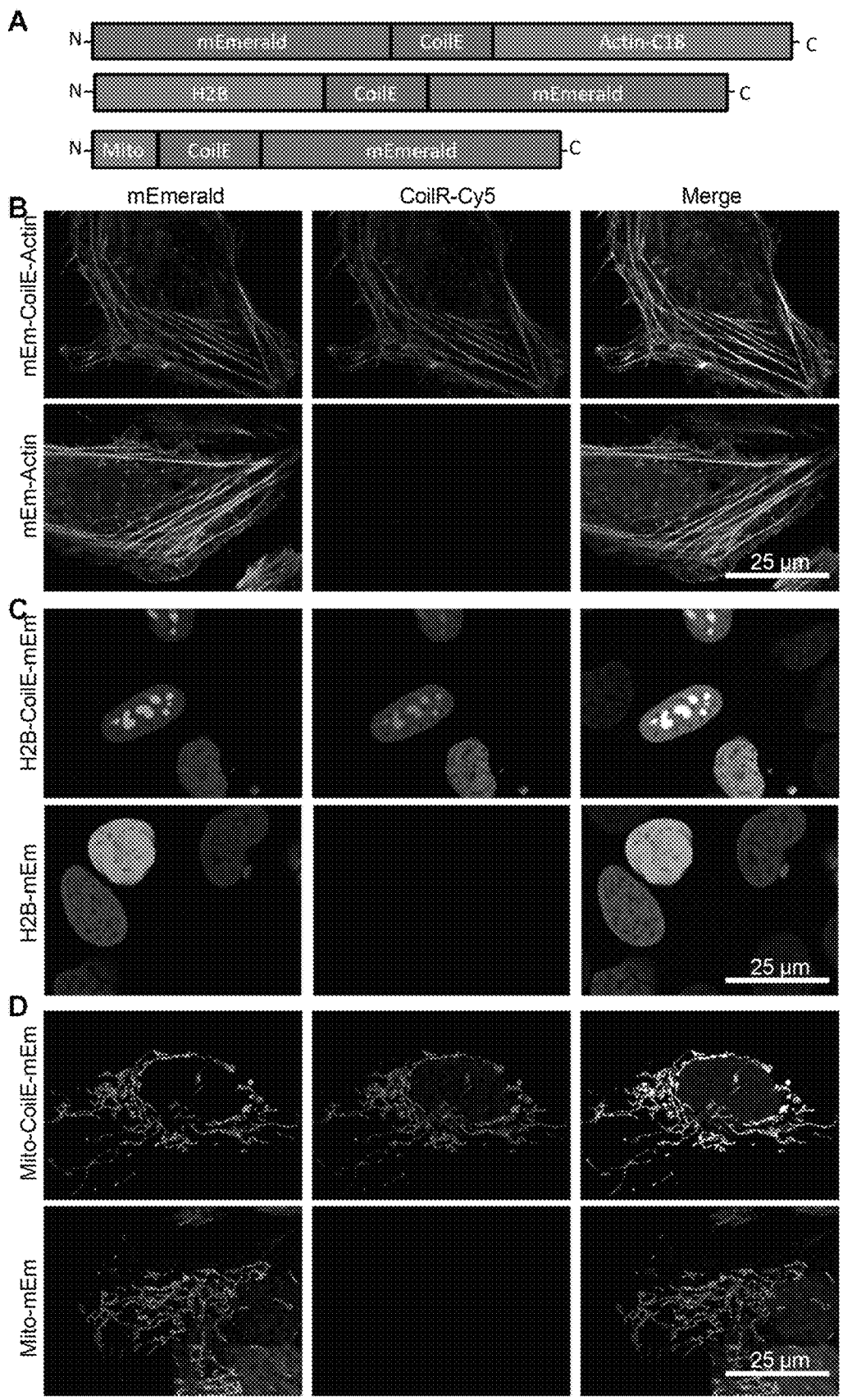
FIGS. 15A, 15B, 15C, and 15D show VIP E/R-tagged proteins localized to sub-cellular structures. VIPER enables intracellular fluorescence tagging in fixed, permeabilized cells. U-2 OS cells were transfected with vectors encoding mEmerald-CoilE-Actin-C18 (FIG. 15B), H2B-6-CoilE-mEmerald (FIG. 15C), or Mito-7-CoilE-mEmerald (FIG. 15D). Post-fixation, cells were permeabilized and targets were detected by treatment with CoilR-Cy5. For untagged target controls (mEmerald-Actin-C18, H2B-6-mEmerald, and Mito-7-mEmerald) no CoilR-labeling was observed. Cy5 is false-colored magenta and mEmerald is false-colored green, with overlapping signal indicated by white in the channel merge. Nuclear stain (Hoechst 33342) is shown in the merge in blue. Gene representation of VIPER-tagged constructs are found in FIG. 15A. These constructs highlight that the CoilE tag can be inserted at an internal site of a protein.

The compatibility of the CoilE/R pair in labeling intracellular and extracellular proteins post-fixation and permeabilization is shown in FIG. 15. To demonstrate the flexibility and the utility of the peptide tags, fluorescent protein constructs, such as mEmerald-actin-C18, H2B-6-mEmerald (a histone protein), and Mito-7-mEmerald (a mitochondrial targeting sequence), were tagged with CoilE for assessing labeling in different cellular compartments. This is the first reported use of coiled-coil peptides to label intracellular protein targets. Tagged constructs were incorporated into a mammalian expression vector, pcDNA3, which features a CMV promoter for constitutive expression. Standard transfection protocols were used to introduce these genes into mammalian tissue culture cells. CoilE was fused internally in the sequence for the organelle-FP markers, between mEmerald and the target protein. The mEmerald green fluorescence served as co-localization markers to compare with VIP labeling.

The CoilE and CoilR peptides were assessed for their ability to label intracellular structures without perturbing normal trafficking and distribution of the tagged proteins. U-2 OS cells were transfected with mEmerald-actin-C18, mEmerald-CoilE-actin-C18, H2B-6-mEmerald, H2B-6-CoilE-mEmerald, Mito-7-mEmerald, and Mito-7-CoilE-mEmerald and fixed with 4% PFA 24 hours after transfection. Cells were then lightly permeabilized and then labeled with 100 nM CoilR-Cy5 in a blocking buffer. Cells were fixed and imaged using with line-scanning confocal microscope. Images showed that Cy5 signal colocalized with mEmerald signal, for actin, histones (H2B), and mitochondria (FIG. 15). In cells expressing the untagged mEmerald constructs, there was no significant Cy5 signal for the same acquisition settings. VIPER labeling was specific, given by the colocalization of features between the VIPER(Cy5) and mEmerald signal. These constructs demonstrated that the CoilE tag could be placed at an internal site of a multidomain protein, such as between mEmerald and Actin-C18 in the mEmerald-CoilE-Actin-C18 construct.

Pearson's correlation coefficients between the mEmerald signal and CoilR-Cy5 was calculated for labeling of each construct, segmented by cell number. The cells labeled as in FIG. 15 at low magnification to capture multiple cells. It was found that for actin-C18, H2B-6, and Mito-7, the Pearson's correlation was 0.97, 0.90, and 0.89 respectively (see FIG. 16).

Figure 18:
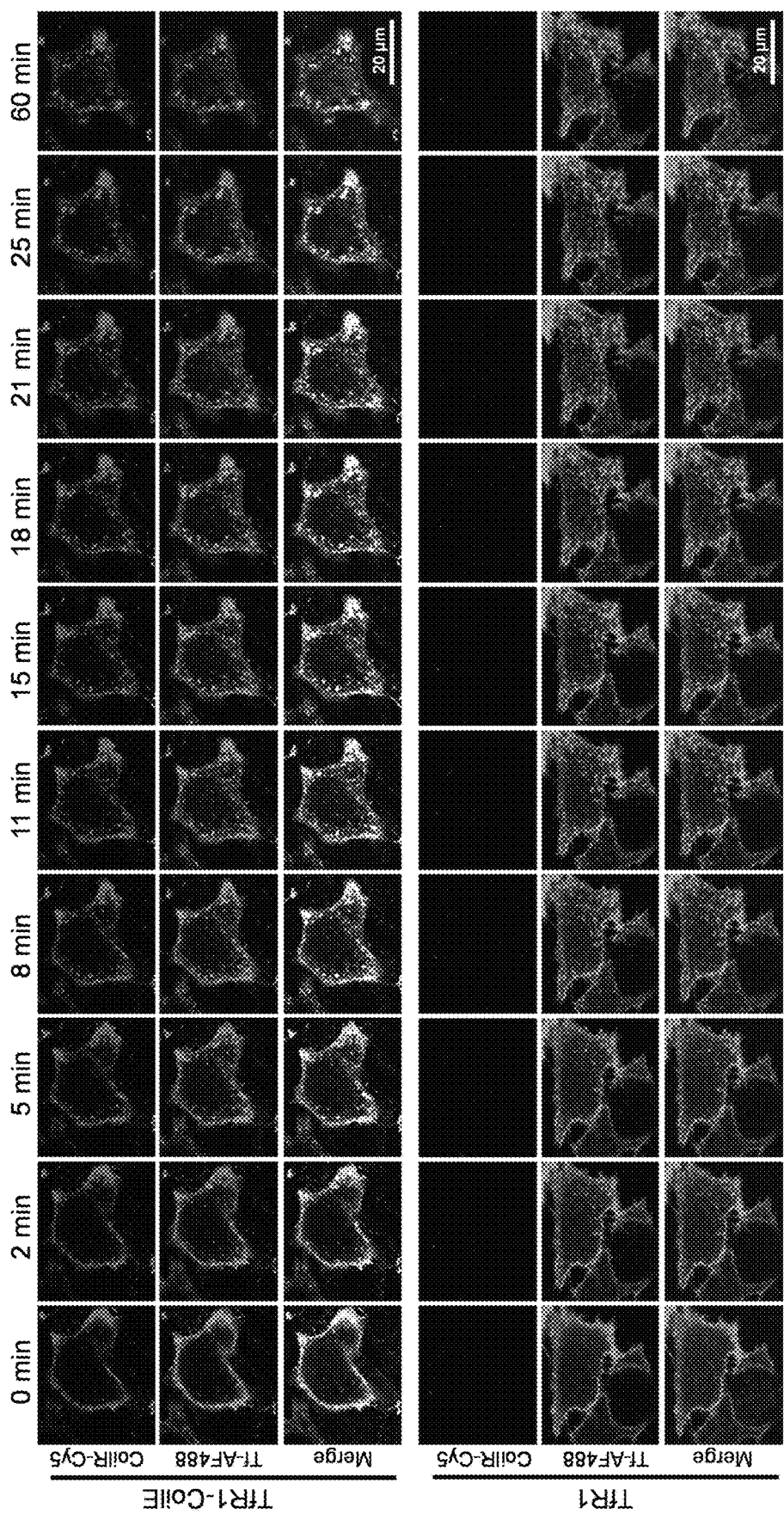
FIG. 18 provides images showing VIP E/R tagged-receptor trafficking can be monitored over time in living cells. CHO TRVb cells expressing TfR1 or TfR1-CoilE were treated cold with 50 µg/mL Tf-AF488 and 500 nM CoilR-Cy5 and washed prior to imaging. Cells were imaged at 37° C. over one hour. Cells were imaged every 2-3 minutes for the first 25 minutes to capture endocytosis of TfR1 and TfR1-CoilE. A final image was taken after an hour at 37° C. incubation. Nuclear stain was taken at the first and last capture. Cy5 was false colored magenta and AF488 was false colored green. Areas where green and magenta overlap appear white in color.

VIP probe peptides are live cell impermeant. This makes them ideal for imaging and tracking receptor internalization. To demonstrate this cells were transfected with TfR1 or TfR1-CoilE. Following transfection, the cells were cooled to 4° C. to halt endocytosis and labeled with CoilR-Cy5 and Tf-AF488 for 30 minutes. Cells were then washed and imaged at 37° C. to allow TfR1 to internalize. A single cell was imaged continuously for an hour, every 2-3 minutes for the first 25 minutes and one last time at the end of an hour (FIG. 18).

Imaging revealed that TfR1 is selectively labeled only on cells expressing TfR1-CoilE, with no CoilR-Cy5 signal in cells expressing untagged TfR1. Both Tf and TfR1 are found on the cell surface at the initial time point and inside the cell at the later time points and Cy5 and AF488 are colocalized. These studies showed that TfR1 internalization could be monitored in live cells over time without perturbing Tf-binding or receptor endocytosis.

VIPER labeling was compared to that of standard fluorescence labeling techniques, namely a fluorescent protein fusion to mCherry and antibody labeling. The cell-membrane impermeance of CoilR allowed us not only to track membrane receptors as in FIG. 18, but VIPER can also differentiate targets separated by time (see FIG. 21). Three different fixed-cell experiments were conducted where it was demonstrated how VIPER labeling TfR1 differs from FP-fusion (FIG. 19), immunolabeling (FIG. 20), and that CoilR probes of different colors can be used together to label to distinct temporal populations of TfR1 (FIG. 21).

Figure 19:
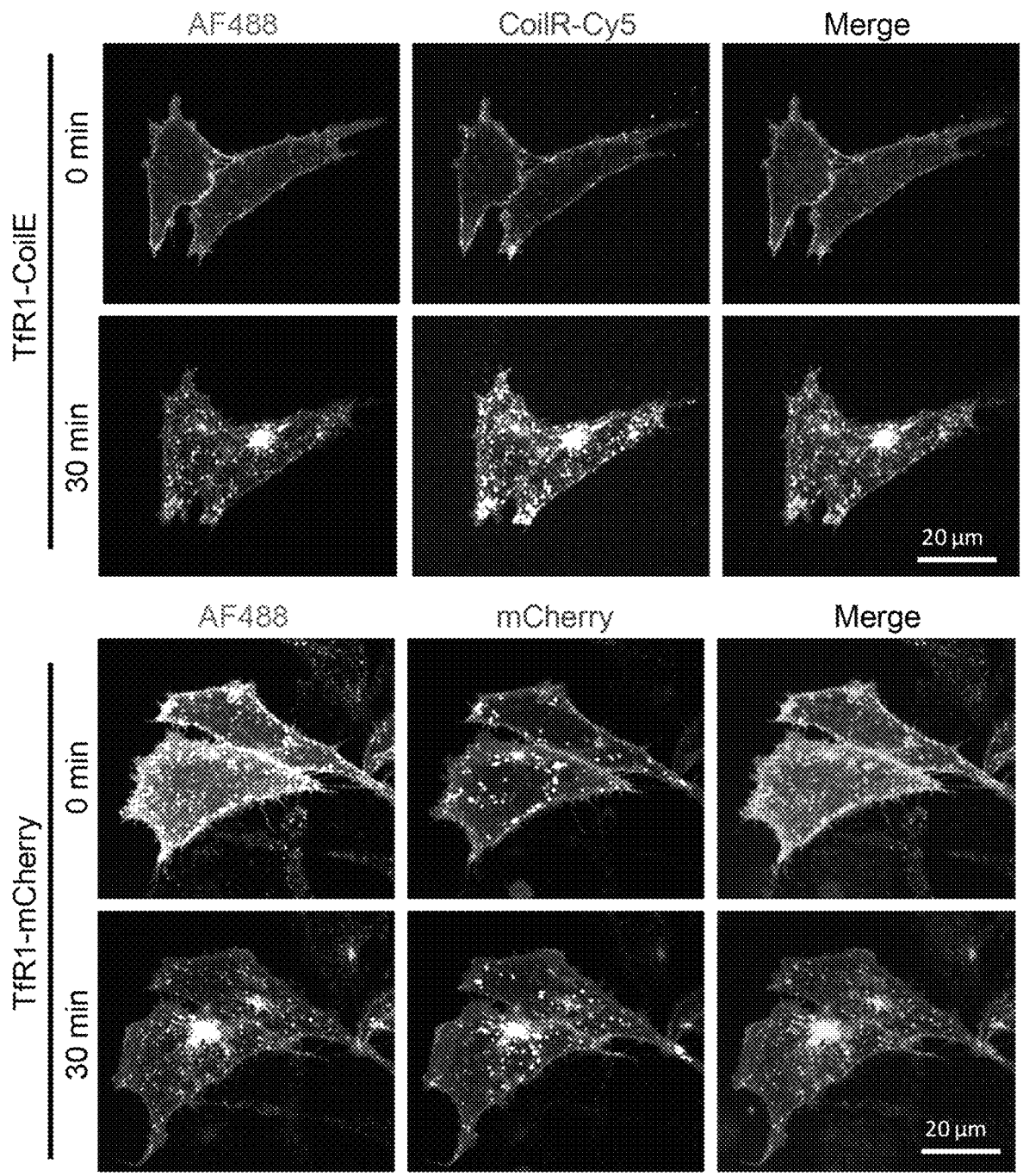
FIG. 19 are images showing a comparison of imaging TfR1 using a fluorescent protein fusion (TfR1-mCherry) compared to VIP E/R (TfR1-CoilE detected by CoilR-Cy5). In both cases, cells were also treated with fluorescent transferrin (Tf-AF488). CHO TRVb cells transfected with TfR1-mCherry or TfR1-CoilE were labeled with Tf-AF488 (50 µg/mL) at 4° C. TfR1-CoilE cells were additionally labeled with 500 nM CoilR-Cy5 for VIP E/R labeling. After labeling, fluorescent cells were imaged after incubation for 0 and 30 min at 37° C. Cells were imaged as confocal slices at 63× magnification.

TfR1 with a C-terminal fusion to red-fluorescent mCherry (TfR1-mCherry) was obtained from Addgene. This construct was transfected to CHO TRVb in order to compare with TfR1 and TfR1-CoilE in fluorescence microscopy with Tf-AF488. Cells expressing TfR1 or TfR1-mCherry were labeled with 50 µg/ml Tf-AF488. Cells expressing TfR1-CoilE were also labeled with 50 µg/ml Tf-AF488 with the addition of 500 nM of CoilR-TAMRA. Labeling was done at 30 minutes at 4° C. to halt endocytosis. Following labeling, cells were washed and fixed immediately afterwards or returned to incubation at 37° C. for 30 minutes and then fixed. Cells were then imaged for blue fluorescence (nuclei), green fluorescence (Tf), and red fluorescence (mCherry or CoilR-Cy5) (FIG. 19).

When the images were processed, brightness and contrast for Tf-AF488 were set the same for all images taken, allowing rough comparison of Tf-AF488 binding. Brightness and contrast were set differently between mCherry and Cy5, despite using the same laser excitation and emission filter setup. In general, mCherry was much brighter than the VIP-Cy5, allowing for a greater dynamic range in imaging.

However, the other important thing to notice is that the Tf-AF488 images for TfR1, TfR1-mCherry, and TfR1-CoilE all indicate that Tf is on the cell surface at 0 min and inside the cell in bright puncta at 30 min. It was thought a fluorescent protein fusion to the receptor portion of TfR1 would interfere with transferrin binding and trafficking, and this does not appear to be the case.

The CoilE and CoilR peptides were further assessed for their ability to label extracellular proteins and track endocytosis of cell membrane receptors. CHO-TRVb cells were transfected with TfR1 or TfR1-CoilE and subsequently treated with CoilR-Cy5 (500 nM) and incubated for 0 or 30 minutes at 4° C., then fixed, then immunolabeled with mouse anti-TfR1 and anti-mouse AF488 (FIG. 20A). At time=0 minutes, TfR1-CoilE on the cell surface is labeled with CoilR-Cy5. After 30 minutes, labeled TfR1-CoilE was trafficked into the cell as expected. This demonstrates the potential for CoilE/R to label distinct populations of proteins and monitor their trafficking by fluorescence microscopy.

Example 14. VIPER and VIP Y/Z Facilitated Labeling of Intracellular Proteins for Analysis by Flow Cytometry The actin- and mitochondria-targeted CoilE-tagged fluorescent protein fusions were used to assess CoilR-Cy5 labeling by flow cytometry (FIG. 17). After transient transfection, single-cell suspensions were fixed and permeabilized, then treated with varying amounts of CoilR-Cy5 probe-peptide. Ideal CoilR-Cy5 labeling of CoilE-tagged actin at concentrations between 10 and 100 nM was observed (see FIG. 17). In addition, short labeling times (ca. 10 minutes at room temperature) appeared sufficient because longer labeling times did not significantly enhance observed fluorescent signal, suggesting the majority of tagged CoilE was labeled in minutes (see FIG. 17).

The VIP Y/Z pair also enabled analysis of cells by flow cytometry (see FIG. 11 and FIG. 25).

Example 15: VIPER can be Used to Track Two Receptor Populations ("Pulse-Chase")

VIPER can be used to track two different populations of receptors at the same time, using different colored CoilR probes (FIG. 21). CHO TRVb cells were transfected with TfR1-CoilE and labeled at 4° C. with 500 nM CoilR-Cy5 to halt endocytosis and to label a "first" population of receptors. Cells were then washed and incubated for 0, 5, 30 and 2 hours at 37° C. and 5% CO2 in F12 media with serum, allowing the "first" population to internalize. Following incubation, cells were labeled at 4° C. with a different color probe peptide, CoilR-BODIPY, labeling a "second" population of receptors. Cells were then washed and fixed prior to imaging. The "first" and "second" TfR1 population signal was colocalized at the 0 min time point, as both populations were at the cell surface, since the "first" population was allowed no time to internalize. For the other time points, we see the "first" TfR1 population in varying stages of endocytosis, while the "second" TfR1 population is always on the cell surface. Cells-transfected with untagged TfR1 and treated in the same manner showed now labeling for either CoilR-Cy5 or CoilR-BODIPY. Therein it was demonstrated that the VIPER technology can be used to different populations of cell membrane target differentiated in time using a dual-color labeling approach (FIG. 21).

Example 16: VIPER can be Used for EM and CLEM

VIP E/R was used for CLEM imaging of TfR1 receptor (FIG. 7). TRVb cells transfected with TfR1 or TfR1-CoilE were plated to indium tin oxide (ITO)-coated coverslips and labeled cold with 100 nM CoilR-biotin and 50 µg/mL Tf-AF488 and then fixed. CoilR-biotin was then detected by 10 nM streptavidin-QD655 and coverslips were imaged on a Corrsight (FEI) with MAPS software. This enabled individual cells' locations to be registered relative to the slide so that they may be reimaged again via SEM. After fluorescent cells were mapped, the coverslips were processed for EM imaging. CLEM of the collected backscatter electrons (BSE) reveal that TfR1-CoilE TRVb label with both Tf-AF488 and QD655, and that imaging the cell surface at 65,000× magnification reveals a dense coating QD655, (white, oblong dots) (FIGS. 7a and 7b). Imaging of a non-fluorescent cell on the same slide (poorly transfected) or TfR1-TRVb showed no QD655 labeling via fluorescence or EM.

This experiment was also repeated for a cell-surface displayed GFP, a target from our previous VIP work (FIG. 22). U-2 OS cells transfected with GFP or CoilE-GFP also displayed selective labeling with CoilR-biotin, which subsequently lead to detection by streptavidin-QD655 visible by fluorescence and EM. The untagged GFP showed no QD655 signal (FIG. 22). Thus we have successfully visualized two different cell surface targets with CLEM through the use of VIPER.

VIP E/R was demonstrated to be a genetically encoded CLEM tag using nanoparticles. VIP E/R is the first genetically encoded EM tag that is not dependent on the precipitation of DAB. There are a variety of functionalized metal and semi-conductor (Qdots) nanoparticles that can be distinguished by size, shape, color or composition. This affords a great degree of flexibility in the EM or correlative light and EM imaging enabled by VIP E/R. All colors of Qdots and a large size range of gold particles are available as streptavidin conjugates, and thus are compatible with our CoilR-biotin probe. CoilR can be conjugated directly to a maleimide-functionalized Nanogold (~1-2 nm gold particle) in a stoichiometric 1:1 labeling and used for direct labeling of targets, without the need for a secondary detection step. Combined with VIP Y/Z or a DAB-precipitating EM tag, VIPER will allow for genetically-encoded multicolor-EM, a technique that was not possible prior to VIP E/R's development.

Example 17: Design of a Shorter, Better Charge Balanced VIP E/R, MiniVIPER

Figure 24A:
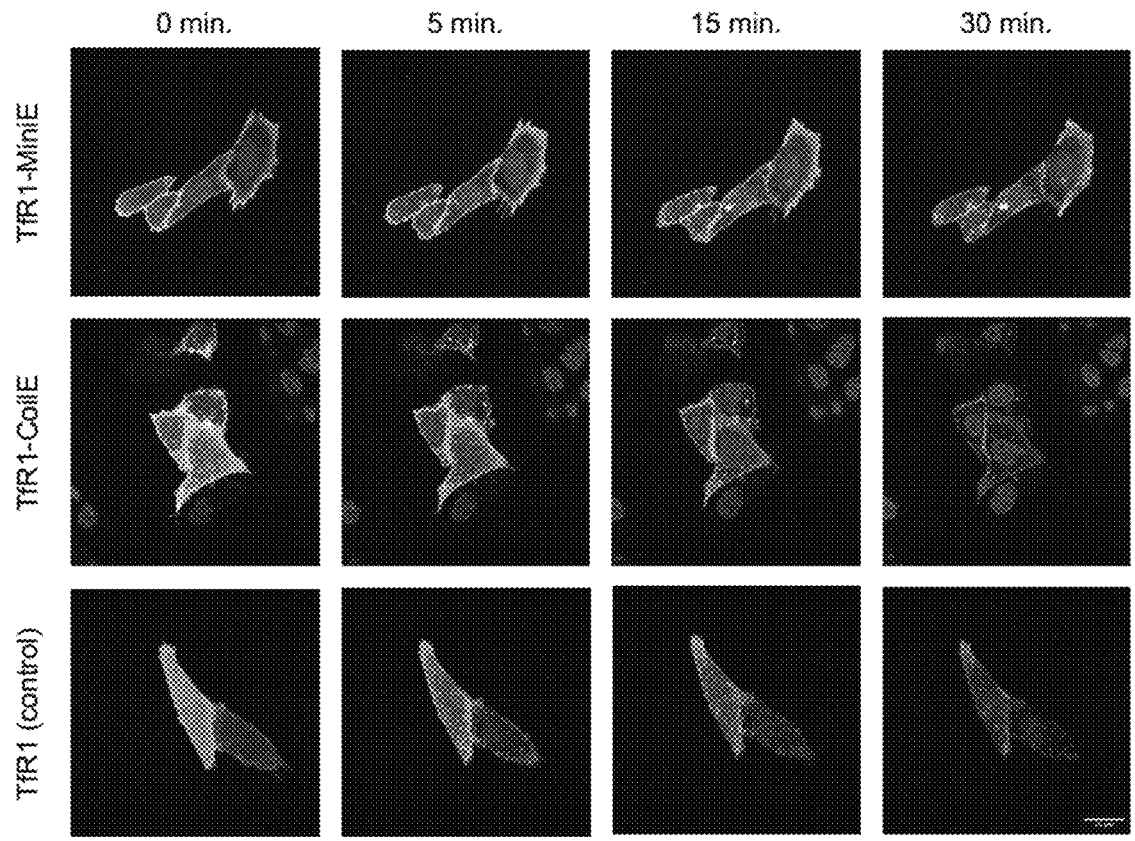
FIG. 24 A and B are fluorescent micrographs comparing VIP E/R labeling with miniVIPER (MiniE and MiniR) labeling of TfR1.
Figure 24B:
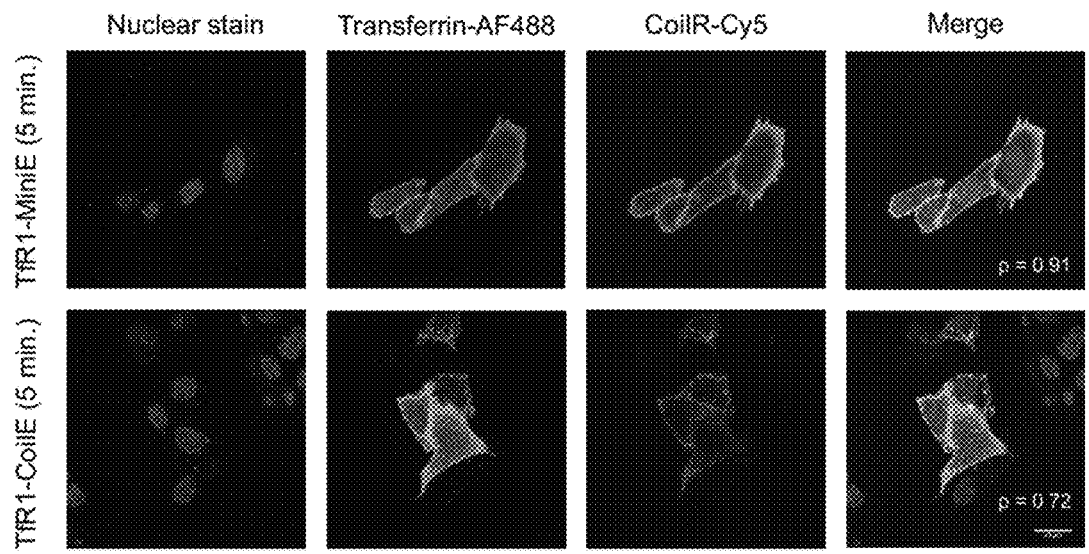

VIP E/R was edited by removing a heptad repeat, and changing key residues in the sequence to maximize affinity, improve dimer interface and create a smaller tag pair with more favorable charge balance for imaging in cells. MiniE (SEQ ID NO:10) and MiniR (SEQ ID NO:9) were created. See Table 1 or 2. TfR1 was tagged at the C-terminus with MiniE. TfR1-MiniE, TfR1-CoilE, and untagged TfR1 were transfected into CHO TRVb and treated with Tf-AF488 and full length CoilR-Cy5 (FIG. 24A and FIG. 24B). TfR1-MiniE bound to CoilR-Cy5, and the signal was colocalized with Tf-AF488. Compared to VIPER, miniVIPER fluorescent micrographs showed brighter Tf-A488 signal and improved colocalization between Tf-AF488 and CoilR-Cy5. This suggests that miniVIPER is a better tag than VIPER; however, VIPER is still effective. MiniVIPER, due to its smaller size and better charge balance, likely showed improved receptor labeling and Tf binding because of a combination of: a higher transfection efficiency, higher protein expression, improved protein folding and trafficking, or a higher affinity for Tf binding.

Example 18: VIPER and VIP Y/Z can be Used for Imaging One Protein Across Multiple Imaging Platforms, Including Across Resolution Scales The technology described herein are unique in its ability to be used across imaging platforms without need for additional cloning. Both VIP E/R and VIP Y/Z were demonstrated to be compatible with imaging on a fluorescence microscope and electron microscope. The VIP-tagged system can be easily moved from platform to platform. A single construct, TfR1-CoilE was imaged via dynamic fluorescence microscopy (FIG. 18, 19, 20, 21, 24), correlative fluorescence and electron microscopy (FIGS. 7a and 7b). A second protein, CoilE-GFP, was also imaged by fluorescence microscopy (FIG. 4) and later by correlative light and EM (FIG. 22). This work was enabled by the use of a quantum dot reporter that is fluorescent and electron dense, therefore the reporter generated contrast in both fluorescence and EM.

Even in absence of reporters with these dual properties, labeled probe peptides can be swapped out for appropriate applications, such as TfR2-CoilZ with CoilY-AF647 for fluorescence imaging (FIG. 6) or CoilR-biotin, detected by streptavidin-gold for TEM (FIG. 8).

Example 19: Use of VIP Tags for Protein Purification and Protein-Protein Interaction "Pull-Down"

VIP probe peptides can be immobilized to a solid support (i.e. agarose, plastic, glass, etc.) and used to purify tagged-protein to the exclusion of other cellular components using affinity binding.

The invention claimed is:

1. A method of visualizing a first protein of interest within a cell, the method comprising:
   (a) expressing a first tagged protein of interest in the cell, said first tagged protein of interest comprising the first protein of interest and a first polypeptide comprising SEQ ID NO: 9, or SEQ ID NO: 10;
   (b) contacting the first tagged protein of interest with a first peptide probe, said first peptide probe comprising a label and a second polypeptide selected from SEQ ID NO: 9 if the first tagged protein of interest comprises SEQ ID NO:10; and SEQ ID NO:10 if the first tagged protein of interest comprises SEQ ID NO:9; and
   (c) visualizing the first label, thereby visualizing the first protein of interest.

2. The method of claim 1, wherein the first tagged protein of interest or the first peptide probe further comprises a cellular localization peptide and/or a purification tag.

3. The method of claim 1, wherein the first label comprises an organic fluorophore, a pH-sensitive fluorophore, an enzyme activated fluorophore, a redox-sensitive fluorophore, a fluorogenic probe, a nonfluorescent protein, an electron dense particle, a fluorescent small molecule, a fluorescent protein, a quantum dot, a gold nanoparticle, biotin, or streptavidin.

4. The method of claim 1, wherein expressing the first tagged protein of interest occurs within a mammalian cell.

5. The method of claim 1, further comprising visualizing a second protein of interest wherein:
   (a) visualizing the second protein of interest comprises immunolabeling, expression of the second protein of interest in conjunction with a protein tag, or a diaminobenzidine (DAB) dependent labeling procedure; and/or
   (b) visualizing the second protein of interest comprises expressing a second tagged protein of interest comprising the second protein of interest and a second polypeptide selected from SEQ ID NO: 9, or SEQ ID NO: 10;
      contacting the second tagged protein of interest with a second peptide probe comprising a label and a second polypeptide selected SEQ ID NO: 9 if the second tagged protein of interest comprises SEQ ID NO: 10; or SEQ ID NO: 10 if the second tagged protein of interest comprises SEQ ID NO: 9; and visualizing the second label, thereby visualizing the second protein of interest; provided that the first label and the second label are distinguishable from one another and provided that the first polypeptide is different from the second polypeptide.

6. The method of claim 5, wherein the second tagged protein of interest or the second peptide probe further comprises a cellular localization peptide and/or a purification tag.

7. The method of claim 5, wherein the second label comprises a fluorescent small molecule, a fluorescent protein, a quantum dot, a gold nanoparticle, biotin, or streptavidin.

8. The method of claim 5, further comprising purifying the second tagged protein of interest.

9. The method of claim 5, wherein expressing the second tagged protein of interest occurs within a mammalian cell.

10. The method of claim 5, wherein visualizing the second label is performed using fluorescence microscopy, electron microscopy, or correlative light and electron microscopy.

* * * * *